(12) United States Patent
Ma et al.

(10) Patent No.: US 10,564,608 B2
(45) Date of Patent: Feb. 18, 2020

(54) ELICITING USER INTERACTION WITH A STIMULUS THROUGH A COMPUTING PLATFORM

(71) Applicant: Disney Enterprises, Inc., Burbank, CA (US)

(72) Inventors: Xun Ma, Chengdu (CN); Jian Fei Ouyang, Shanghai (CN); Mei Shan Zhou, Shanghai (CN); Hui Li, Shanghai (CN); Ju-Hsin Chao, Shanghai (CN); Hsin Yi Yueh, Shanghai (CN); Brian Dai, Shanghai (CN); Tong Yong Liu, Beijing (CN); Chen Hu Wu, Shanghai (CN)

(73) Assignee: Disney Enterprises, Inc., Burbank, CA (US)

( * ) Notice: Subject to any disclaimer, the term of this patent is extended or adjusted under 35 U.S.C. 154(b) by 0 days.

(21) Appl. No.: 15/977,460

(22) Filed: May 11, 2018

(65) Prior Publication Data
US 2019/0349464 A1    Nov. 14, 2019

(51) Int. Cl.
*G04G 13/02*    (2006.01)
*H04M 1/725*    (2006.01)
(Continued)

(52) U.S. Cl.
CPC .............. *G04G 13/02* (2013.01); *G04G 11/00* (2013.01); *G04G 13/023* (2013.01); *G06F 3/017* (2013.01);
(Continued)

(58) Field of Classification Search
CPC .. G06F 3/017; G06F 3/04847; G06F 3/04883; G06F 3/167; A61M 21/00; A61M 2021/0083; G04G 13/02; G04G 11/00
See application file for complete search history.

(56) References Cited

U.S. PATENT DOCUMENTS

| 4,332,019 | A | * | 5/1982 | Lynches | ................. | G04B 23/03 368/12 |
| 4,430,006 | A | * | 2/1984 | Jetter | ................... | G04G 13/021 368/262 |

(Continued)

FOREIGN PATENT DOCUMENTS

| EP | 2688275 | 1/2014 |
| WO | 2013093712 | 6/2013 |
| WO | 2013187874 | 12/2013 |

OTHER PUBLICATIONS

Google Play Store, I Can't Wake Up! Alarm Clock—Android Apps on Google Play, Sep. 23, 2015, https://play.google.com/store/apps/details?id=com.kog.alarmclock, retrieved on May 30, 2019 using https://web.archive.org (Year: 2015).*

(Continued)

*Primary Examiner* — Nicholas Ulrich
(74) *Attorney, Agent, or Firm* — Esplin & Associates, PC

(57) ABSTRACT

One aspect of this disclosure relates to presenting a user with a stimulus to elicit user interaction with a task on a computing platform associated with the user. The stimulus may be presented on the computing platform when a set of triggering criteria is satisfied. The stimulus includes a task for the user to complete. The stimulus prompts the user to complete the task. The task includes a set of task criteria for completion. Responsive to the user satisfying the set of task criteria, the user is presented with one or more options to modify the stimulus. The user may be continuously prompted by the stimulus until the set of task criteria is satisfied.

18 Claims, 9 Drawing Sheets

(51) Int. Cl.
*G06F 3/0488* (2013.01)
*G04G 11/00* (2006.01)
*G06F 3/01* (2006.01)
*G06F 3/0484* (2013.01)
*A61M 21/00* (2006.01)

(52) U.S. Cl.
CPC ........ *G06F 3/0488* (2013.01); *G06F 3/04847* (2013.01); *G06F 3/04883* (2013.01); *H04M 1/72544* (2013.01); *A61M 21/00* (2013.01); *A61M 2021/0083* (2013.01)

(56) References Cited

U.S. PATENT DOCUMENTS

| | | | | |
|---|---|---|---|---|
| 5,095,468 | A * | 3/1992 | Sato | A63F 9/0096 368/262 |
| 5,189,648 | A | 2/1993 | Cooper | |
| 5,442,600 | A | 8/1995 | Kutosky | |
| 5,926,442 | A * | 7/1999 | Sirhan | G04B 23/03 368/262 |
| 5,928,133 | A | 7/1999 | Halyak | |
| 6,009,048 | A | 12/1999 | Raesz | |
| 6,888,779 | B2 | 5/2005 | Mollicone | |
| 6,928,031 | B1 | 8/2005 | Kanevsky | |
| 7,506,035 | B1 * | 3/2009 | Lu | G04G 15/006 368/10 |
| 7,743,340 | B2 | 6/2010 | Horvitz | |
| 7,990,807 | B2 * | 8/2011 | Li | G04G 13/021 368/262 |
| 8,195,194 | B1 * | 6/2012 | Tseng | H04M 1/72569 455/456.1 |
| 9,152,131 | B2 | 10/2015 | Mokhnatkina | |
| 9,703,269 | B2 * | 7/2017 | Yang | H04M 1/72566 |
| 2008/0259742 | A1 | 10/2008 | Tadanori | |
| 2008/0309616 | A1 * | 12/2008 | Massengill | A61B 3/113 345/156 |
| 2009/0046541 | A1 * | 2/2009 | Chou | G04G 13/021 368/262 |
| 2009/0086585 | A1 | 4/2009 | Chou | |
| 2009/0175134 | A1 * | 7/2009 | Yang | G04G 13/021 368/73 |
| 2013/0033436 | A1 * | 2/2013 | Brinda | G06F 3/0488 345/173 |
| 2013/0044072 | A1 * | 2/2013 | Kobayashi | H04M 1/0237 345/173 |
| 2014/0026105 | A1 * | 1/2014 | Eriksson | G04G 13/026 715/863 |
| 2014/0127665 | A1 * | 5/2014 | Arai | G06Q 50/20 434/362 |
| 2015/0091811 | A1 | 4/2015 | Hombert | |
| 2015/0277388 | A1 * | 10/2015 | Almudafier | G04G 15/00 368/11 |
| 2016/0163181 | A1 * | 6/2016 | Levy | G04G 13/02 340/539.13 |

OTHER PUBLICATIONS

Kog Creations, I Can't Wake Up! Alarm Clock, Nov. 15, 2015, http://kogcreations.com/android/, retrieved on May 30, 2019 using https://web.archive.org (Year: 2015).*
Gaddget, Best Alarm App: I Can't Wake Up! Review, Sep. 25, 2015, https://www.youtube.com/watch?v=GCASrntUz2w, Screenshots created by examiner on May 30, 2019. (Year: 2015).*
Podotreeus, Introducing Mission Alarm Clock!, Oct. 24, 2011, https://www.youtube.com/watch?v=RINmbbQQbGs, screenshot created by examiner on May 30, 2019. (Year: 2011).*
Game Up Alarm Clock, Game Up Alarm Clock, Sep. 4, 2013, https://www.youtube.com/watch?v=yly4Juq8mcw, screenshot created by examiner on May 30, 2019. (Year: 2013).*
Anna Green, An Alarm Clock App That Wakes You Up With Games, Mental Floss, Jan. 22, 2016 [retrieved from the internet on Jul. 9, 2017] http://mentalfloss.com/article/74197/alarm-clock-app-wakes-you-games (8 pgs).

* cited by examiner

ELICITING USER INTERACTION WITH A STIMULUS THROUGH A COMPUTING PLATFORM

FIELD OF THE DISCLOSURE

The present disclosure relates to presenting a user with a stimulus through a simulated physical space displayed on a computing platform to elicit user interaction.

BACKGROUND

Alarm clocks, including digital alarms clocks presented through a mobile phone, are designed to ring at a set time and often have a function of snooze. To stop or snooze the alarm, a user may tap on a snooze or stop button on the phone's screen, or utilize physical buttons. However, in some instances when the alarm goes off, the user, being awakened by the alarm clock abruptly and being extremely sleepy, might unconsciously turn off the alarm and thus sleep past the time they are supposed to get up.

SUMMARY

One aspect of this disclosure relates to presenting a user with a stimulus to elicit user interaction with a task on a computing platform associated with the user. The stimulus may be presented on the computing platform at a predetermined time. The stimulus may comprise of visual content and/or audible notifications. The visual content may include a depiction of a simulated physical space, one or more virtual objects, and/or other virtual content. The virtual objects may be positioned throughout a topography of the simulated physical space. The task may be presented on the simulated physical space via the virtual objects. The task may include a set of task criteria for completion, and/or other information. The audible notifications may notify the user of the task presented. The audible notification may include a vocal notification, an audio cue associated with the task, and/or other audible notification. The stimulus may be ceased when the set of task criteria for completing the task is satisfied by the user. The user may modify the stimulus when the set of task criteria for completing the task is satisfied by the user.

In some implementations, a system configured to present a stimulus to elicit user interaction with a task may include one or more servers, one or more computing platforms, one or more external resources, and/or other components. Users may access the system via the computing platforms, and/or other devices. In some implementations, the server(s) may include one or more of electronic storage, one or more physical processors, and/or other components. In some implementations, the one or more physical processors may be configured by machine-readable instructions. Executing the machine-readable instructions may cause the one or more physical processors to present the stimulus through the simulated physical space on the computing platform. The machine-readable instructions may include one or more computer program components. The one or more computer program components may include one or more of a configuration component, a presentation component, an input component, a determination component, a reconfiguration component, and/or other components.

The configuration component may be configured to determine one or more settings of a stimulus presented on a computing platform. The one or more settings of the stimulus may include one or more of trigger information, virtual content information, task information, and/or other information of the one or more settings of the stimulus. The trigger information may define a set of triggering criteria for presenting the stimulus and/or other information. The virtual content information may define audio and/or visual content of the stimulus. The task information may define a task of the stimulus, a set of task criteria for completing the task, a level of difficulty of the tasks, and/or other information of the task. The one or more settings may be determined based on one or more of user input from one or more users, real-world events, virtual world events, user information from a third-party application, and/or information. The user input may be from a user associated and/or not associated with the computing platform.

The presentation component may be configured to effectuate presentation of the stimulus on the computing platform. The stimulus may be presented on the computing platform according to the one or more settings of the stimulus. The presentation component may be configured to determine whether the set of triggering criteria has been satisfied. Responsive to the set of triggering criteria being satisfied, the presentation component may be configured to effectuate presentation of the stimulus. The presentation of the stimulus includes presentation of the audio and/or visual content including a depiction of a simulated physical space, one or more virtual objects, an audible notification, and/or other content. The virtual objects may be positioned throughout the topography of the simulated physical space. A task may be presented on the simulated physical space via the virtual objects. The audible notification may notify the user of the stimulus presented.

The input component may be configured to obtain user input information defining user inputs, and/or other information. The input component may obtain the user input from the computing platform, and/or other devices. The input component may be configured to obtain user input information defining user inputs while the stimulus may be presented on the computing platform. The user input may include user inputs to modify the one or more settings of the stimulus, user inputs to modify the stimulus, the user's attempt to satisfy the set of task criteria, and/or other user inputs. User input may comprise one or more of a gesture input, one or more of a touch gesture input, one or more of a controller input, an audio input, a text input, and/or other inputs. A touch gesture input may be received through a touch-enabled display of the computing platform.

The determination component may be configured to determine whether the one or more criteria of the set of task criteria has been satisfied. The determination component may be configured to determine whether the one or more criteria of the set of task criteria has been satisfied based on user inputs. The determination component may be configured to determine whether the user input satisfies the one or more criteria of the set of task criteria. The determination component may be configured to determine whether the user attempts to satisfy the one or more criteria of the set of task criteria. The determination component may determine whether the user inputs satisfy the one or more criteria of the set of task criteria by comparing the user input with the one or more criteria of the set of task criteria.

The reconfiguration component may be configured to modify the stimulus based on whether the one or more criteria of the set of task criteria has been satisfied. Responsive to the user attempting and/or not attempting to satisfy the one or more criteria of the set of task criteria, the reconfiguration component may be configured to modify the stimulus based on the one or more settings of the stimulus.

The modification may include modifying audio levels of the audio content, modifying the level of difficulty of the task, and/or other modifications. Responsive to the set of task criteria being satisfied, the reconfiguration component may be configured to cease the presentation of the stimulus, facilitate modification of the stimulus by the user, and/or modify the stimulus in other ways.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description and are not intended as a definition of the limits of the invention. As used in the specification and in the claims, the singular form of "a," "an," and "the" include plural referents unless the context clearly dictates otherwise.

DETAILED DESCRIPTION

Figure 1:
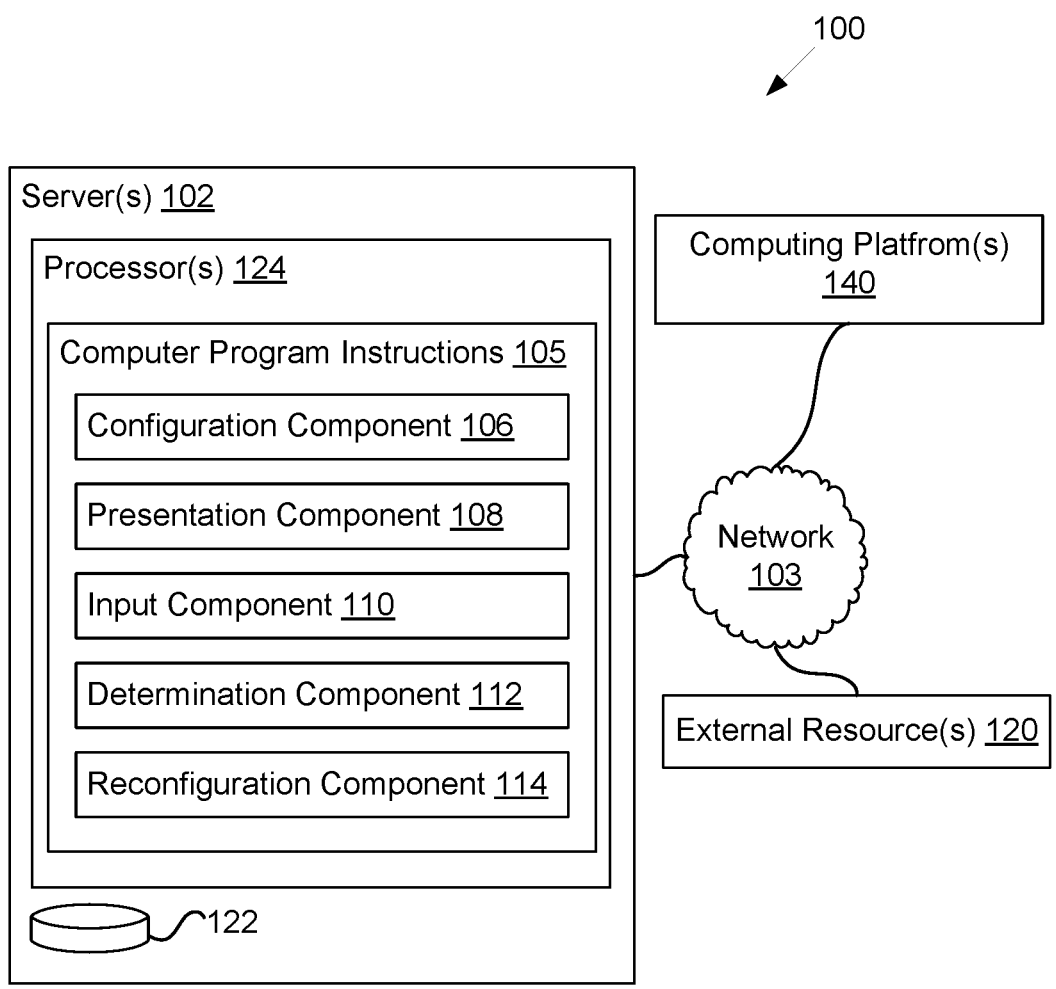
FIG. 1 illustrates a system configured to present a stimulus through a simulated physical space on a computing platform to elicit user interaction, in accordance with one or more implementations.

FIG. 1 illustrates a system 100 configured to present a stimulus to elicit user interaction with a task. The task may be one or more of a game, a puzzle, an interaction, and/or other activities for the user to accomplish. The stimulus may be presented to a user on a computing platform at a predetermined time. The stimulus may include a presentation of visual and/or audio content. The visual content may include a depiction of one or more of the game, the puzzle, the interaction, and/or other virtual content. The virtual objects may be positioned throughout the topography of the simulated physical space. The audio content may include audio content of one or more of the game, the puzzle, the interaction, the other activities, an audible notification, and/or other audio content. The virtual objects positioned throughout the topography of the simulated physical space may be elements of the task and/or elements for completing the task.

As is illustrated in FIG. 1, system 100 that may be configured to present a stimulus to elicit user interaction with a task may include one or more servers 102, one or more computing platforms 140, one or more external resource 120, and/or other components. Users may access system 100 via computing platform(s) 140, and/or other devices. Users may communicate with server(s) 102 via computing platform(s) 140, and/or other devices. Server(s) 102 and/or computing platform(s) 140 may access external resource(s) 120, and/or other components of system 100.

Computing platform(s) 140 may be one or more of a mobile computing device (such as one or more of a smartphone, smartwatch, etc.), a personal computer, a network of computers, a wearable computing device (such as a head-mounted computing device), a game console, a smart home device (such as a virtual assistance device and/or a smart speaker), and/or other computing platforms. The smart home device may be configured to control one or more systems in a home and/or building. The one or more systems in the home may include a lighting system, an air conditioning system, a heating system, and/or other home systems. Computing platform(s) 140 may include one or more of one or more input devices, one or more displays, one or more sensors, one or more audio output devices, and/or other components. Is noted that computing platform(s) 140 may represent an individual computing platform and/or more than one computing platform that may be similarly configured as described herein.

The input devices may include one or more of a computer mouse, a keyboard, a game controller, a touch-enabled input device, a motion capture device, an imaging device, and/or other input devices. The input devices may be removably coupled to computing platform(s) 140. The input devices may be integrated with computing platform(s) 140.

The touch-enabled input device may be a touch screen and/or other devices. The touch screen may include one or more of a resistive touchscreen, a capacitive touchscreen, a surface acoustic wave touchscreen, an infrared touchscreen, an optical imaging touchscreen, an acoustic pulse recognition touchscreen, and/or other touchscreens. The touch-enabled input device may be configured to generate output signals conveying touch gesture information defining touch gesture inputs of the user.

The motion capture device may include one or more image sensors, motion sensors, depth sensors, and/or other sensors. The motion capture device may be configured to generate output signals conveying motion information defining movements of a user.

The imaging device may include one or more image sensors, infrared sensors, depth sensors, and/or other sensors for imaging. The imaging device may be configured to generate output signals conveying visual information defining visual content of a user. The visual content of the user may include movements made by the user. The visual content may be a video/video clip of the user. An imaging device may be a camera or a series of cameras.

The displays may be a device configured to effectuate presentation of visual content. The displays include one or more of a touch-enabled display (e.g., the touchscreen), an LCD display, a LED display, an OLED display, a projector, and/or other displays.

The sensors of computing platform(s) 140 may include one or more image sensors, audio sensors, and/or other sensors. The audio output devices of computing platform(s) 140 may be one or more of a speaker, a headphone, an earbud, and/or other audio output devices.

In some implementations, an image sensor may be configured to generate output signals conveying visual information, and/or other information. The visual information may define visual content within a field of view of the image sensor and/or other content. The visual content may include depictions of real-world objects and/or surfaces. The visual content may be in the form of one or more of images, videos, and/or other visual information. The field of view of the image sensor may be a function of a position and an orientation of a computing platform. In some implementations, an image sensor may comprise one or more of a photosensor array (e.g., an array of photosites), a charge-coupled device sensor, an active pixel sensor, a complementary metal-oxide semiconductor sensor, an N-type metal-oxide-semiconductor sensor, and/or other devices.

In some implementations, an audio sensor may be configured to generate output signals conveying audio information, and/or other information. The audio information may define audio from a user of the audio sensor (e.g., utterances of the user), audio around the user (such as ambient audio), and/or other information. In some implementations, an audio sensor may include one or more of a microphone, a micro-electro-mechanical microphone, and/or other devices.

In some implementations, a depth sensor may be configured to generate output signals conveying depth information within a field of view of the depth sensor, and/or other information. The depth information may define depths of real-world objects and/or surfaces, and/or other information. A field of view of the depth sensor may be a function of a position and an orientation of a computing platform. In some implementations, the depth information may define a three-dimensional depth map of real-world objects and/or a user. In some implementations, the depth sensor may comprise of one or more ultrasound devices, infrared devices, light detection and ranging (LiDAR) devices, time-of-flight cameras, and/or other depth sensors and/or ranging devices. In some implementations, the infrared devices may include one or more infrared sensors. The infrared sensors may generate output signals conveying the depth information.

In some implementations, a repository of information defining the stimulus may be available via server(s) 102 and/or computing platform(s) 140. The information defining the stimulus may be stored in one or more electronic storage(s) 122, non-transitory storage media, and/or other storage media. The repository of the information defining the stimulus may be a data structure configured to store information defining the stimulus for a computing platform. The repository of the information defining the stimulus may comprise a computer-readable medium. The data structure configured to store information defining the information defining the stimulus may be a single database or multiple databases.

In some implementations, the repository of information defining the stimulus may include information defining one or more settings of the stimulus. The one or more settings of the stimulus may define when the stimulus may be presented to computing platform(s) 140, the content of the stimulus, and/or other information. The one or more settings of the stimulus may be defined by one or more of trigger information, virtual content information, task information, and/or other information of the one or more settings of the stimulus. The trigger information may define a set of triggering criteria and/or other information. The triggering criteria may specify when the stimulus may be presented to computing platform 140 and/or other information. The virtual content information may define audio and/or visual content of the stimulus and/or other information. The task information may define a task of the stimulus, a set of task criteria for completing the task, a level of difficulty of the task, and/or other information of the task. The one or more settings of the stimulus of the may be predetermined, determined by a user, and/or modified by the user.

The set of triggering criteria may include criteria for specifying one or more points in time to present the stimulus, one or more events that may enable the presentation of the stimulus, one or more geolocations where the stimulus may be presented, one or more users who may enable the presentation of the stimulus, one or more physical conditions of the user that may enable the presentation of the stimulus, and/or other criteria and/or other information. The set of triggering criteria may be predetermined, determined by a user, and/or modified by the user.

The points in time to present the stimulus may be a single point in time and/or multiple points in time. The points in time may be points in time in the real-world and/or a virtual world. For example, a point in time in the real-world may be 8 am and/or other times in pacific standard time (PST). A point in time in the virtual world may be a point in time according to a time zone/time system of the virtual world. The multiple points in time may specify a duration of time. For example, the multiple points in time may specify points in time between two points of time, points in time after a point in time, points in time before a point in time, and/or other points in time. By way of non-limiting example, a criterion of the set of triggering criteria may specify that the stimulus may be presented at 8 am PST. A criterion of the set of triggering criteria may specify that the stimulus may be presented between 8 am to 10 am PST.

The events that may enable the presentation of the stimulus may be a real-world event, a virtual-world event, and/or other events. The presentation of the stimulus may be enabled at the beginning of the event, during the event, and/or after the events. The real-world event may be an occurrence that takes place in the real world. For example, the real-world event may be a holiday, a concert, a change of season, a particular weather, an appointment date, and/or other real-world events. The virtual-world event may be an occurrence that takes place in the virtual world. For example, the virtual-world event may be an in-game event and/or other virtual-world events.

The geolocations where the stimulus may be presented may be a location in the real world. The geolocations may include a single geolocation and/or multiple geolocations. In some implementations, the multiple geolocations may be specified by an area in the real world. By way of non-limiting example, a criterion of the set of triggering criteria may specify a location in the real world, such as the user's house, bedroom, at a landmark, at a specific geolocation, and/or other locations, where a stimulus may be presented. The stimulus may be presented when the user is at the location in the real world.

The users who may enable the presentation of the stimulus may be a user who may remotely enable the presentation of the stimulus on computing platform(s) 140. For example, the user may be the user associated and/or not associated with computing platform(s) 140, a friend of the user, and/or other users who may remotely trigger the presentation of the stimulus on computing platform(s) 140.

The physical conditions of the user may be one or more biological conditions of the user. The physical conditions of the user may be specified by a user's heart rate, an oxygen level, a hydration level, a stress level, a sleep quality, a blood sugar level, and/or other physical conditions. A criterion of the set of triggering criteria may specify that a stimulus may be presented when specific physical conditions of the user may be detected. For example, a criterion of the set of triggering criteria may specify that a stimulus may be presented when the user experiences a heart rate of over 100 beats per minute and/or other physical conditions.

The visual content of the stimulus may include a depiction of a game, a puzzle, an interaction, and/or other activities. The completion of the game, the puzzle, the interaction, and/or the other activities may be the task associated with the stimulus. The game, the puzzle, the interaction, and/or the other activities may be part of a virtual reality content, an augmented reality content, and/or other content. The game, the puzzle, the interaction, and/or the other activities may include a depiction of a simulated physical space, a depiction of one or more virtual objects, and/or other visual content. The virtual objects may be positioned throughout the topography of the simulated physical space. The virtual objects and/or the simulated physical space may be part of the virtual reality content, the augmented reality content, and/or other content. The virtual objects may include one or more of a virtual entity, a virtual structure, game/puzzle elements, and/or other virtual objects. The simulated physical space, the virtual object, and/or the other visual content may make up elements of the game, the puzzle, the interaction, and/or the other activities.

The simulated physical space may be in a three-dimensional space, two-dimensional space, and/or other simulated physical spaces. The simulated physical space may depict an environment. In some implementations, the simulated physical space may include a head-up display (HUD) overlaid on the three-dimensional, two-dimensional space, and/or other simulated physical spaces. A HUD may comprise of one or more of a mini-map, menu, one or more application information readings, and/or other information. In some implementations, the simulated physical space may make up the environment of the virtual reality content, the augmented reality content, and/or other content.

The virtual entity may include a depiction of a character/avatar, a group of characters/avatars, a vehicle, and/or other entities. In some implementations, the character/avatar and/or group of characters/avatars may occupy/ride the vehicle. The character/avatar may be a depiction of a fictional character and/or a real-world character. The vehicle may be one or more of a motorized vehicle, flying vehicle, and/or vehicles. The virtual entity may be controlled by a user, preprogrammed behaviors, an artificial intelligence, and/or other controlling systems and/or entities.

The virtual structure may include a depiction of a building, a store, a landmark, and/or other virtual structures. In some implementations, the virtual structure may be a representation of a real-world structure. In some implementations, the virtual structure may be a virtual-world structure. In some implementations, the virtual structure may include the virtual entity, and/or other virtual content. For example, the virtual entity may be within and/or occupy the virtual structure.

The game/puzzle element may include one or more of an item, a widget, the virtual entity, the virtual structure, and/or other elements that make up a game/puzzle. In some implementations, the item may be a virtual weapon/tool, virtual food, virtual gadget, and/or other virtual items/goods. In some implementations, the widget may be an interface component for controlling/interacting with elements within the game/puzzle. A widget may include one or more buttons, and/or other components.

The virtual objects may be static or dynamic. For example, the virtual objects may be positioned in a fixed location (e.g., static) or move about locations in the topography of the simulated physical space (e.g., dynamic). In some implementations, the virtual structures and/or virtual entities may be static. In some implementations, the virtual entities may be dynamic. In some implementations, the virtual structures may be static, and the virtual entities may be dynamic.

The audio content of the stimulus may include audio content of the game, the puzzle, the interaction, the other activities, an audible notification, and/or other audio content. The audio content of the game, the puzzle, the interaction, and/or the other activities may include a soundtrack, a sound clip, conversations between entities within the game, and/or other audio content. The soundtrack may be a song, an ambient/background noise, and/or other audio content. The sound clip may be a part/segment of the soundtrack. The audio notification may notify the user that the stimulus may be presented and/or prompt the user to interact with the presented stimulus. The audible notification may include verbal communication, an audio cue, an audio alert, and/or other audible notifications. The verbal communication may include a speech, a conversation, and/or other verbal communication. The audio cue may be an audio signal that prompts the beginning of the stimulus and/or an occurrence in the stimulus.

The audible notification may be based on user information defining the user associated with the computing platform(s) 140's history, geolocation, events, and/or other information. In some implementations, the user's history may include the user's purchase history, travel history, Internet browsing history, conversation history, medical history, education history, interests/preferences, and/or other information relating to the user's history. The user's history may be a user's history in the real world and/or the virtual world. In some implementations, the user's geolocation may include the user's present geolocation, the user's proximity to a geolocation and/or landmark, the user's predicted travel route, the user's proximity to a geolocation and/or landmark on the predicted travel route and/or other information relating to the user's geolocation.

The verbal communication may communicate information relating to the user's history, geography, events, and/or other information. In some implementations, the verbal communication may communicate information based on purchases made by the user, locations visited by the user, events attended by the user, conversations the user had, websites visited, and/or other information of the user in the real world. For example, the verbal communication may inform the user of a sale based on the user's purchase history and/or travel history, the weather based on the user's geolocation, and/or other information. The events may be the real-world event and/or of the virtual world event (e.g., a game event). The medical history may include a history of the user's physical conditions, weight, height, and/or other information relating to the user's medical history.

The audio cue may signal the start of the presentation of the stimulus and/or other information. For example, the audio cue may effectuate an audio signal prior to the start of the presentation of the stimulus such that a user may be notified that the stimulus may be about to occur or may be occurring. An audio cue may signal an occurrence in the stimulus. For example, the audio cue may effectuate an audio signal such that the user may be notified that an occurrence of the stimulus has occurred. The occurrence in the stimulus may include success and/or failure of the user's attempt to satisfy a criterion of the set of task criteria, a change in the set of task criteria, a change in the level of difficulty of the task, and/or other occurrences in the stimulus.

The task may be an activity and/or set of activities for the user to perform and/or interact with. A set of task criteria may determine when a task may be completed. The task may include a game, a puzzle, an interaction, and/or other activities. The task may be to play a game, solve a puzzle, interact with an entity, and/or other tasks. The game may be a video game including one or more of an online game, an offline game, a single player game, a multiplayer game, a local co-op game, and/or other games.

The game may include one or more objectives/goals for the user to achieve. The one or more objectives/goals of the game may be to perform an activity in the real-world, perform an activity in a virtual world, and/or other objectives/goals. For example, an activity in the real-world may include visiting a landmark, making a purchase, attending an event (such as a music festival), and/or other activities. An activity in the virtual world may include beating a game boss, delivering an in-game item, and/or other activities. The set of task criteria may specify the objectives/goals of the game.

A puzzle may include one or more objectives/goals for the user to achieve. The puzzle may propose a problem and/or challenge for a user to solve. For example, the proposed problem and/or challenge may be a word search, a math problem, a matching problem, a riddle, and/or other problems. The puzzle may be part of the game. The set of task criteria may specify the objectives/goals of the puzzle.

The interaction with the entity may include one or more objectives/goals for the user to achieve. The interaction with the entity may include an interaction with a virtual entity, an interaction with a real-world entity, and/or other interactions. The interaction with the entity may include engaging in a conversation with the entity, engaging in an activity with the entity, and/or other interactions. Interaction with a virtual entity may include interaction with a virtual entity (such as a game avatar or NPC) in a video game or presented on a computing device. Interaction with a real-world entity may include interaction with a person, an animal, a robot, and/or other real-world entities. The set of task criteria may determine when the interaction with the entity may be satisfied.

The task may be presented on a display including depictions of a simulated physical space of a simulated-environment on the display of computing platform(s) 140. The simulated physical space may be an environment in which the task takes place. The task may include manipulating the virtual objects positioned through the topography of the simulated physical space. For example, in the game, the simulated physical space may be a gameplay environment of the game, and the virtual objects may be the game elements of the game. In a puzzle, the simulated physical space may be an environment to present the puzzle, and the virtual objects may be elements for solving the puzzle. In an interaction with a virtual entity, the simulated physical space may be an environment the virtual entity resides, and the virtual objects may include the virtual entity.

The set of task criteria may specify criteria/conditions for completing the task. The set of task criteria may be used to determine when the task may be complete. For example, if the set of task criteria is satisfied, then the task may be complete. Individual tasks may have individual sets of task criteria. The set of task criteria for a task may be based on the task. For example, in a word search task, a set of task criteria for the task may be to find a certain number of words. In a game where a user may be required to fix a virtual entity with virtual objects (such as tape), a set of task criteria for the task may be to place the virtual objects on the virtual entity to fix the virtual entity. In a math problem task, a set of task criteria for the task may be to input a number that solves the math problem. The set of task criteria of the tasks may be predetermined, determined by a user, and/or modified by a user.

In some implementations, one or more criterion of the set of task criteria may require a user to input information, the user to select the one or more virtual objects, the user to interact with the one or more virtual objects, the user to interact with one or more real-world entities, an occurrence of an event, and/or other criteria. The input information may include one or more of a text input, a controller input, an audio input, a touch gesture input, a body gesture input, and/or other inputs.

For example, the selection of the one or more virtual objects may include selection of virtual objects positioned throughout the topography of the simulated physical space. The user interaction with the one or more virtual objects may include a conversation with a virtual entity, playing a game with a virtual entity, reposition the virtual objects, and/or other interactions with the one or more virtual objects. The interaction with the real-world entities may include a conversation with a real-world entity, playing a game with the real-world entity, and/or other interactions. The occurrence of the event may be a real-world event, a virtual world event, and/or other events. The text input may be an input of one or more words, phrases, and/or other text inputs. The controller input may be an input of one or more button presses, button presses in a specific order, and/or other controller inputs. The audio input may be an input of one or more audio signals, such as speaking one or more words, phrases, sentences, and/or other audio input. The touch gesture input may include making one or more touch gestures on a touch-enabled device of computing platform(s) 140. The body gesture input may include making one or more movements with a body part of the user.

The occurrence of the event may or may not be caused by the user. In some implementations, the set of task criteria may require the occurrence of the event to be caused by the user. An occurrence of the event caused by the user may be an event that occurred in reaction to a user's actions. For example, the set of task criteria may require a virtual object to move to a location within the simulated physical space. The user may move the virtual object to the location within the simulated physical space, or the user may instruct a virtual entity to move the virtual object to the location within the simulated physical space. The set of task criteria may be satisfied when the virtual entity, without instructions from the user, moves the virtual object to the location within the simulated physical space. In some implementations, the criteria of the set of task criteria may require a user to provide audio inputs including one or more of speaking one or more words, singing one or more songs, speaking for a certain duration, speaking with a certain audio level (e.g., volume), and/or other provide other audio inputs.

In some implementations, a criterion of the set of task criteria may require a virtual entity within a game to be at a specific location within the topography of a simulated physical space. The criterion may be satisfied by the user if the user moves the virtual entity to the specific location within the topography of the simulated physical space. The criterion may be satisfied if the virtual entity may be moved by another virtual entity to the specific location within the topography of the simulated physical space. The criterion may be satisfied if the virtual entity, without instructions from the user, moves to the specific location within the topography of the simulated physical space.

The level of difficulty of the tasks may specify the level of complexity of the criterion of the set of task criteria. The greater the level of difficulty of the tasks, the greater the level of complexity of the criterion of the set of task criteria. In some implementations, level of difficulty of the tasks may specify an amount of criteria in a set of task criteria. For example, a greater level of difficulty of the tasks may specify a greater number of criteria in the set of task criteria. In some implementations, the level of difficulty of the tasks may specify a level of complexity of the criteria in the set of task criteria. For example, a greater level of difficulty of the tasks may specify a criterion that may be more challenging than a criterion with a lesser level of difficulty. An association between the level of difficulty of the tasks and/or the level of complexity of the criterion of the set of task criteria may be predetermined.

In some implementations, the level of complexity of the criterion of the set of task criteria may be based on the amount of time the user previously took to satisfy a previous set of task criteria. The amount of time the user previously took to satisfy a previous set of task criteria may indicate if the level of complexity of the criterion of the set of task criteria may be too difficult. If the amount of time the user previously took to satisfy the previous set of task criteria was greater than average, the level of complexity of the criterion of the set of task criteria may be decreased. If the amount of time the user previously took to satisfy the previous set of task criteria was less than average, the level of complexity of the criterion of the set of task criteria may be increased.

In some implementations, the level of complexity of the criterion of the set of task criteria may be based on a number of attempts the user took to satisfy the previous set of criteria. The number of attempts the user took to satisfy the previous set of task criteria may indicate if the level of complexity of the criterion of the set of task criteria may be too difficult. If the number of attempts the user took to satisfy the previous set of task criteria was greater than average, the level of complexity of the criterion of the set of task criteria may be decreased. If the number of attempts the user took to satisfy the previous set of task criteria was less than average, the level of complexity of the criterion of the set of task criteria may be increased.

By way of non-limiting illustration, a criterion of a set of task criteria with a first level of difficulty may require a user to click a button, and a criterion of a set of task criteria with a fifth level of difficulty may require a user to click multiple buttons in a specific order. The user may be required to perform a series of mental calculation to determine the specific order.

Server(s) 102 may include one or more of electronic storage(s) 122, one or more physical processors 124, and/or other components. In some implementations, processor(s) 124 may be configured by machine-readable instructions 105. Executing machine-readable instructions 105 may cause processor(s) 124 to present a stimulus to elicit user interaction with a task. Machine-readable instructions 105 may include one or more computer program components. The one or more computer program components may include one or more of a configuration component 106, a presentation component 108, an input component 110, a determination component 112, a reconfiguration component 114, and/or other components.

Configuration component 106 may be configured to identify and/or determine one or more settings of the stimulus presented on computing platform(s) 140. Configuration component 106 may identify and/or determine the one or more settings of the stimulus defined by the trigger information, the virtual content information, the task information, and/or other information of the one or more settings of the stimulus. Configuration component 106 may obtain the information defining the one or more settings of the stimulus from electronic storage(s) 122, non-transitory storage media, and/or other storage media. Configuration component 106 may obtain the information defining the one or more settings of the stimulus from external resource(s) 120 and/or other devices.

Configuration component 106 may identify the one or more settings of the stimulus presented on computing platform(s) 140 based on the information obtained from electronic storage(s) 122, non-transitory storage media, and/or other storage media. Configuration component 106 may identify the one or more settings of the stimulus presented on computing platform(s) 140 based on the information obtained from external resource(s) 120 and/or other devices. Configuration component 106 may identify when the stimulus may be presented based on the trigger information and/or other information. Configuration component 106 may identify the audio and/or visual content presented based on the virtual content information and/or other information. Configuration component 106 may identify the task of the stimulus based on the task information and/or other information.

Configuration component 106 may determine the one or more settings of the stimulus presented on computing platform(s) 140 based on user input and/or other information. Configuration component 106 may obtain the user input from an input device of computing platform(s) 140, external resource(s) 120, and/or other devices. The user input may specify instructions to modify the one or more settings of the stimulus. Modification of the one or more settings of the stimulus may include alteration of the visual and/or audio content of the stimulus, altering when the stimulus may be presented, altering the task of the stimulus, and/or altering other information of the one or more settings of the stimulus. Configuration component 106 may determine modifications to the one or more settings based on the user input and/or other information. The user input may specify instructions to modify the trigger information, the virtual content information, the task information, and/or other information of the one or more settings of the stimulus.

The user input may be from a user associated and/or not associated with computing platform(s) 140 and/or other devices. Configuration component 106 may be configured to obtain input information defining user input from an input device of computing platform(s) 140 and/or an input device of another computing platform. For example, configuration component may be configured to obtain input information captured by a touch screen device of computing platform(s) 140 or input information captured by a touch screen of another computing platform. Configuration component 106 may be configured to obtain user input information obtained by input component 110 and/or other components.

In some implementations, one or more options to modify the one or more settings of the stimulus may be presented on computing platform(s) 140. In some implementations, the user may select the one or more options to modify the one or more settings of the stimulus on computing platform(s) 140. The options to modify the one or more settings of the stimulus may be predetermined, determined by the user, and/or modified by the user.

The options to modify the one or more settings of the stimulus may be defined by the information defining the one or more settings of the stimulus. For example, options to modify when the stimulus may be presented may be defined by the trigger information, options to modify the visual and/or audio content of the stimulus may be defined by virtual content information, options to modify the task of the stimulus may be defined by the task information, and/or other options to modify other elements of the stimulus may be defined by other information defining the one or more settings of the stimulus. The user may select the one or more options to modify the one or more settings of the stimulus on the input device of computing platform(s) 140. Based on the user's selection of the options to modify the one or more settings of the stimulus, configuration component 106 may determine the one or more settings of the stimulus for presentation.

In some implementations, the user input may modify the trigger information to alter the time when the stimulus may be presented to computing platform 140. For example, the user input may modify the trigger information such that the stimulus may be presented at 9 am instead of 8 am. The user input may modify the virtual content information to alter the audio and/or visual content of the stimulus presented to computing platform 140. For example, the user input may modify the soundtrack presented by the audio content, the information communicated by the verbal communication, the appearance of the virtual object and/or simulated physical space, and/or other content. The user input may modify the task information to alter the task included in the stimulus, the set of task criteria, the level of difficulty, and/or other information relating to the task. For example, the user input may modify the task information such that a game may be presented instead of a puzzle. The user input may modify the set of task criteria such that a different set of task criteria may be required to satisfy the set of task criteria. The user input may modify the level of difficulty such that there may be fewer criteria in the set of task criteria.

Presentation component 108 may be configured to effectuate presentation of the stimulus. Presentation component 108 may be configured to effectuate presentation of the stimulus on computing platform(s) 140 and/or other devices. Presentation component 108 may be configured to facilitate presentation of the stimulus on a display of computing platform(s) 140. The stimulus may be presented as an application on computing platform(s) 140. Presentation component 108 may be configured to facilitate presentation of the stimulus on computing platform(s) 140 when the set of triggering criteria has been satisfied.

Presentation component 108 may be configured to determine whether the set of triggering criteria has been satisfied. For example, if the set of triggering criteria requires the time to be 9 am for the stimulus to be presented, presentation component 108 may be enabled to present the stimulus at 9 am. If the set of triggering criteria requires a holiday for the stimulus to be presented, presentation component 108 may be enabled to present the stimulus at the start, during, and/or before the end of the holiday.

In some implementations, presentation component 108 may be configured to obtain information generated by sensors, input devices, third-party application, and/or other devices to determine whether the set of triggering criteria has been satisfied. Presentation component 108 may be configured to obtain information generated by the sensors of computing platform(s) 140, the input devices of computing platform(s) 140, and/or other components of computing platform(s) 140. Presentation component 108 may be configured to obtain information from external resource(s) 120, and/or other devices.

For example, if a triggering criterion requires a user to be at a specific geolocation, presentation component 108 may be configured to obtain information defining the user's geolocation to determine if the triggering criterion is satisfied. If a triggering criterion specifies when the stimulus may be presented on computing platform(s) 140, presentation component 108 may be configured to obtain information defining a real-world time and/or other information. If a triggering criterion specifies an event when the stimulus may be presented on computing platform(s) 140, presentation component 108 may be configured to determine if the event may be occurring and/or occurred. If a triggering criterion specifies a user's physical condition for when the stimulus may be presented on computing platform(s) 140, presentation component 108 may be configured to obtain information defining the user's physical condition and/or other information.

Responsive to the set of triggering criteria being satisfied, presentation component 108 may be configured to effectuate presentation of the stimulus. Presentation component 108 may be configured to transmit information to computing platform(s) 140 to facilitate the presentation of the stimulus on computing platform(s) 140. Presentation component 108 may be configured to effectuate presentation of the stimulus on the display (e.g., a touch-enabled input device), the audio output devices (e.g., a speaker), and/or other components of computing platform(s) 140. The stimulus may be presented on computing platform(s) 140 according to the one or more settings of the stimulus.

In some implementations, presentation component 108 may be configured to effectuate presentation of the stimulus on a device associated with computing platform(s) 140. For example, presentation component 108 may be configured to effectuate presentation of the stimulus on the smart home device (e.g., smart speakers), and/or other devices associated with computing platform(s) 140 (e.g., a smartphone and/or other devices). The device associated with computing platform(s) 140 may communicate with computing platform(s) 140 via a wireless and/or wired network. In some implementations, presentation component 108 may be configured to effectuate presentation of the stimulus on the device associated with computing platform(s) 140 contemporaneously in time with computing platform(s) 140. In some implementations, presentation component 108 may be configured to effectuate presentation of the same stimulus on the device associated with computing platform(s) 140 and computing platform(s) 140. In some implementations, presentation component 108 may be configured to effectuate presentation of different stimulus on the device associated with computing platform(s) 140 and computing platform(s) 140. The stimulus may be presented on the device associated with computing platform(s) 140 according to the one or more settings of the stimulus.

In some implementations, presentation component 108 may be configured to control the one or more systems in the home associated with the smart home device and/or other devices. Presentation component 108 may be configured to facilitate control of the lighting system, the air conditioning system, the heating system, and/or other home systems. In some implementations, presentation component 108 may be configured to facilitate a dimming or brightening of lights, or turning on or off the lights in the lighting system. For example, presentation component 108 may be configured facilitate turning on the lights of the lighting system when the stimulus is presented. In some implementations, presentation component 108 may be configured to facilitate the opening or closing of window shades. In some implementations, presentation component 108 may be configured to facilitate a change in temperature in the air conditioning system and/or heating system. For example, presentation component 108 may be configured facilitate an increase in temperature in the air conditioning system and/or heating system when the stimulus is presented.

The presentation of the stimulus may include presentation of the visual content, audio content, and/or other content defined by the virtual content information. The presentation of the visual content may include a depiction of the game, the puzzle, the interaction, and/or other virtual content. The presentation of the visual content may include presentation of a depiction of the simulated physical space, one or more virtual objects, and/or other visual content on the displays (e.g., the touchscreen display) of computing platform(s) 140.

A task defined by the task information may be presented on the stimulated physical space. The one or more virtual objects positioned throughout the topography of the simulated physical space may be elements for completing the task. The position of the virtual objects within the topography of the simulated physical space may be determined based on the virtual content information. In some implementations, the position of the virtual objects within the topography of the simulated physical space may be modified by a user. For example, a task (e.g., a game) may involve putting a first virtual entity in a first virtual structure. A user may manipulate the first virtual entity, such that the first virtual entity may be placed in the first virtual structure.

Figure 7:
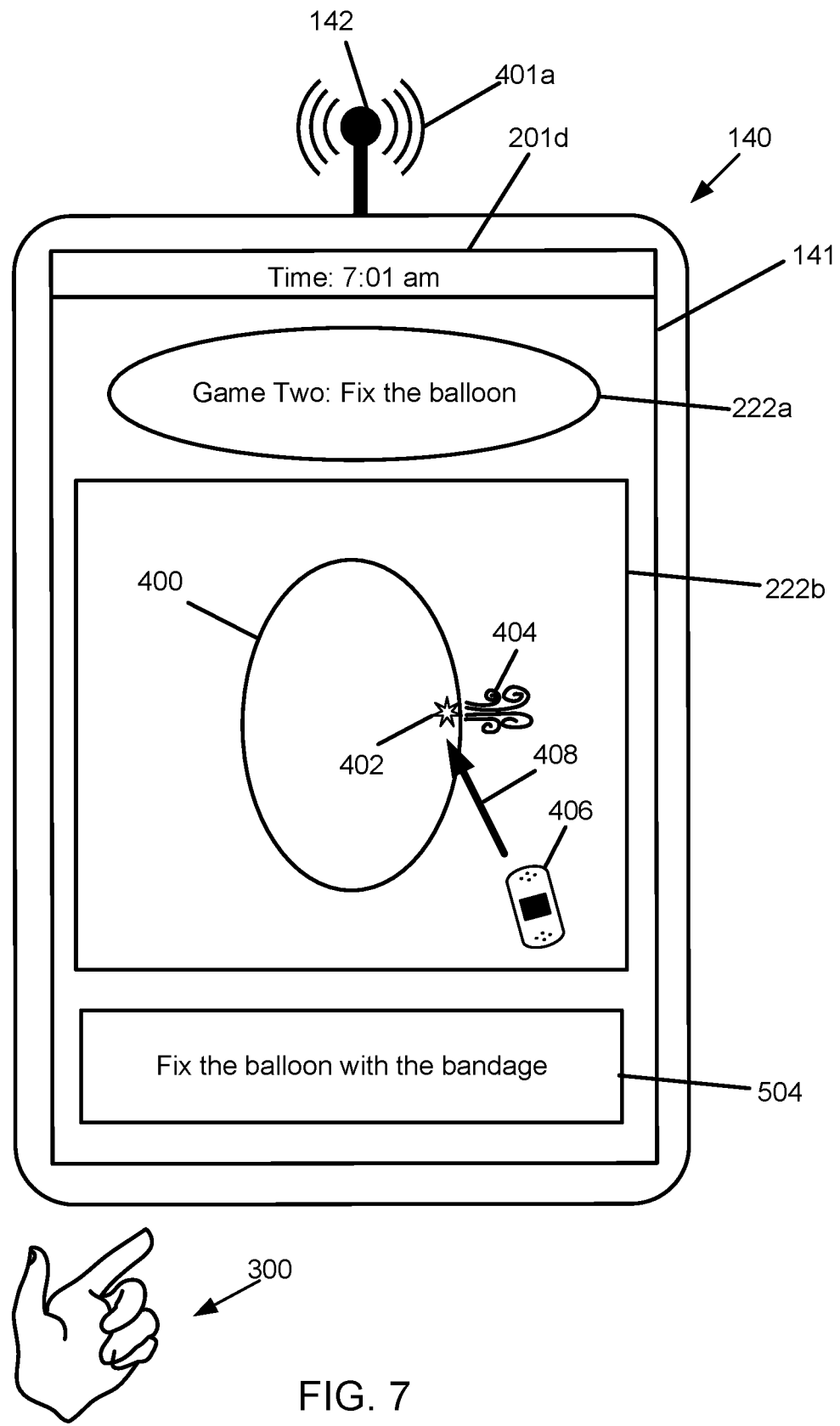
FIG. 7 illustrates a depiction of a second stimulus including a task having a set of task criteria presented on a computing platform, in accordance with one or more implementations.
Figure 8:
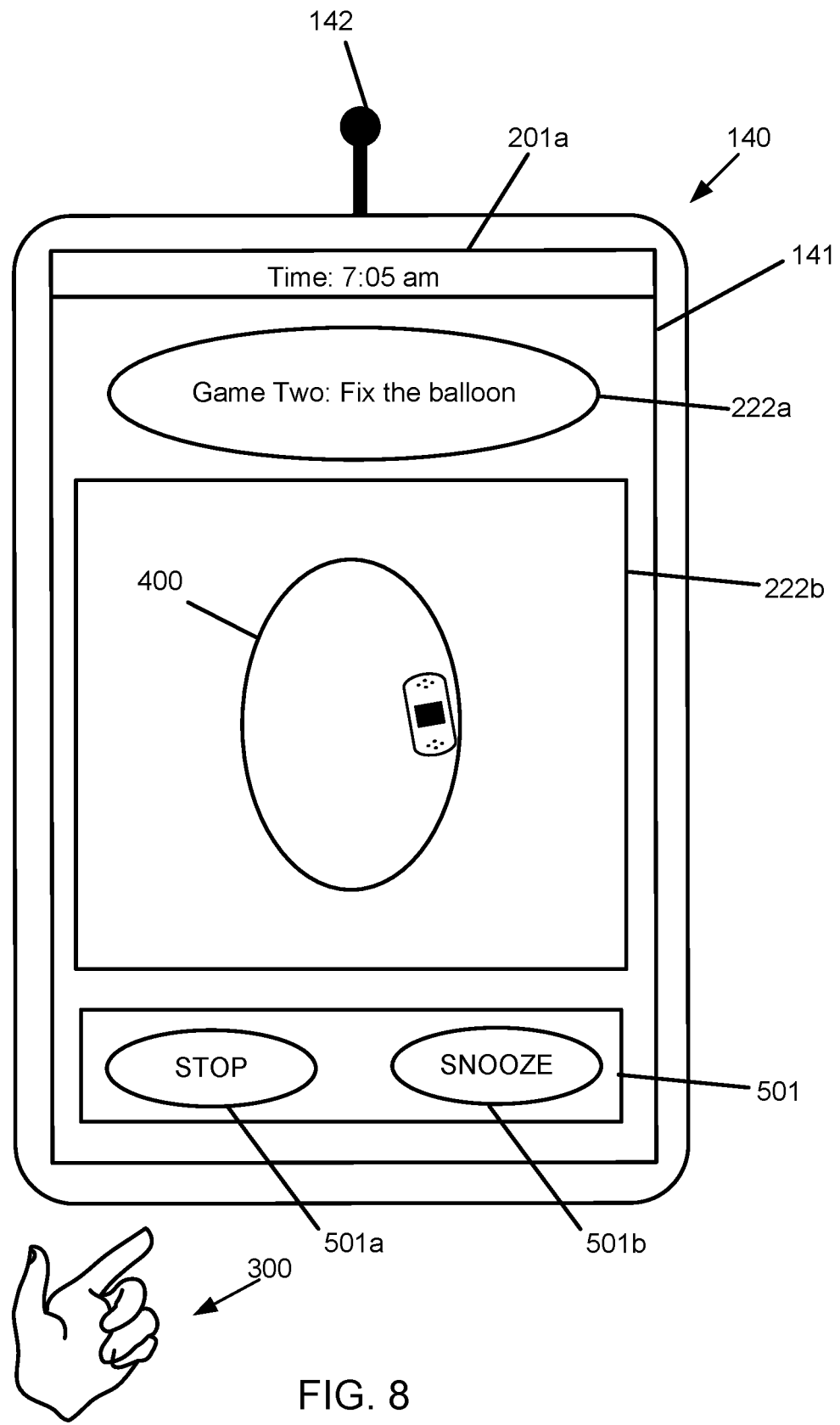
FIG. 8 illustrates a depiction of a user satisfying the set of task criteria of the task of the second stimulus presented on a computing platform, in accordance with one or more implementations.

In some implementations, the presentation of the stimulus may include the presentation of one or more virtual entities. The virtual entities may be positioned throughout the topography of the simulated physical space. The virtual entity may attempt to engage the user in an activity. For example, the virtual entity may be damaged and/or broken. The virtual entity may be presented with one or more holes to indicate the damage. The virtual entity may require the user to place one or more virtual objects (e.g., virtual object of tape) on the virtual entity to repair the damage (as illustrated in FIGS. 7 and 8). The number of holes may increase over time if the user does not engage in the activity of fixing the virtual entity. The number of holes may decrease as the user engages in the activity of fixing the virtual entity.

The presentation of the audio content may include presentation of the audible notification, the soundtrack, the sound clip, and/or other audio content. The audio content may be presented by the audio output device (e.g., a set of speakers) of computing platform(s) 140. In some implementations, the soundtrack and/or the sound clip may be presented as background audio and/or other audio information. The audible notification may have a greater audio intensity compared to the background audio.

In some implementations, the background audio may be presented contemporaneously with the stimulus. In some implementations, the background audio may be presented at predetermined times of the stimulus. For example, the background audio may be presented at the start of the stimulus, when the user engages with the task (e.g., provides user input), when the user satisfies a criterion of the set of task criteria, when the user satisfies the set of task criteria, when the user attempts but fails to satisfy the set of task criteria, and/or other events that occur during the stimulus. In some implementations, the background audio may be presented for a set duration of time. For example, the background audio may be presented for a predetermined duration of time at the start of the stimulus. In some implementations, the background audio may be presented until the user engages with the task (e.g., provides user input) or when the user satisfies a criterion of the set of task criteria. For example, the background audio may be presented at the start of the stimulus and may be ceased when the user satisfies the set of task criteria.

In some implementations, the background audio may be background music and/or other audio content. The background audio may be presented when the virtual entity appears within the topography of the simulated physical space. The background audio may change based on the condition of the virtual entity and/or the stimulus. For example, the background audio may be a first song when the virtual entity does not require the user to engage in the activity of fixing the virtual entity. The background audio may be a second song when the virtual entity requires the user to engage in the activity of fixing the virtual entity.

In some implementations, the audible notification may be presented contemporaneously with the stimulus. In some implementations, the audible notification may be presented at predetermined times of the stimulus. The audible notification may be presented at predetermined intervals of time of the stimulus. For example, the audible notification may be presented at the start of the stimulus, when the user engages with the task (e.g., provides user input), when the user satisfies a criterion of the set of task criteria, when the user satisfies the set of task criteria, when the user attempts but fails to satisfy the set of task criteria, and/or other events that occur during the stimulus. In some implementations, the audible notification may be presented for a set duration of time. For example, the audible notification may be presented for a predetermined duration of time at the start of the stimulus. In some implementations, the audible notification may be presented when the user does not engage with the task (e.g., provides user input) or when the user does not satisfy a criterion of the set of task criteria. The audible notification may be presented at the start of the stimulus and may be ceased when the user satisfies the set of task criteria.

In some implementations, the audible notification may include the virtual entity verbally communicating with the user. The verbal communication may communicate information about the real world to the user. The verbal communication may communicate information based on information defining the user's history, geolocation, events, and/or other information. For example, the virtual entity may verbally communicate information about a sale based on the user's purchase history and/or travel history, the weather based on the user's geolocation, and/or other information. The verbal communication may prompt the user to engage in the activity.

The virtual entity may prompt the user to engage in the activity by stating the activity for the user to participate in. The virtual entity may prompt the user to engage with the activity by calling the user's name, shouting at the user, and/or communicating other information to prompt the user to engage with the activity. The virtual entity may continuously prompt the user to engage in the activity until the user responds. The user may respond by engaging the activity and/or providing a user input.

In some implementations, the virtual entity may be part of the activity. For example, a game may require the user to fix the virtual entity by placing virtual objects (such as virtual object of tape) on the virtual entity. The virtual entity may be presented with one or more holes and may effectuate audio signal of leaking gas to prompt the user to fix the virtual entity. The virtual entity may use verbal communication to ask the user to use the virtual objects to fix the virtual entity. Responsive to the user fixing the virtual entity by placing the virtual objects on the virtual entity, the virtual entity may be presented with fewer holes, and/or the audio signal of leaking air may cease. Responsive to the user not responding to the verbal communication, the virtual entity may increase the audio volume of the verbal communication and demand the user to use the virtual objects to fix the virtual entity. The audio signal of leaking air may increase in volume responsive to the user not engaging the activity.

In some implementations, presentation component 108 may be configured to alter the audio intensity of the audio content. Presentation component 108 may be configured to increase the audio intensity of the audio content if no user input is detected by computing platform(s) 140. Presentation component 108 may be configured to increase the audio intensity of the audio content if the set of task criteria is not satisfied. For example, user not reacting to the stimulus (such that the virtual entity prompting the user to engage in the activity of fixing the virtual entity) in a predetermined duration of time (e.g., not providing user input), presentation component 108 may increase the audio intensity of the audio content. Responsive to the set of task criteria not being satisfied in a predetermined duration of time, presentation component 108 may increase the audio intensity of the audio content. Presentation component 108 may be configured to increase the audio intensity of the audio content over time to encourage the user to react to the stimulus and/or satisfy the set of task criteria.

In some implementations, presentation component 108 may be configured to alter the audio content. Presentation component 108 may be configured to alter the audio content when no user input is detected at a predetermined duration of time. Presentation component 108 may be configured to alter the audio content when the set of task criteria is not satisfied after a predetermined duration of time. Presentation component 108 may be configured to alter the audio content when a criterion in the set of task criteria may be satisfied and/or may be not satisfied. For example, presentation component 108 may be configured to the audio content when a criterion in the set of task criteria in the puzzle is satisfied. Presentation component 108 may be configured to alter the audio content based on how the set of task criteria may be satisfied. For example, based on an order in which the criterion in the set of task criteria may be satisfied, presentation component 108 may be configured to alter the audio content differently. The altered audio content may be a first audio content, and the unaltered audio content may be a second audio content. The first audio content and the second audio content may be distinct from one another.

For example, the virtual entity may change the way it asks or tells the user to engage in the activity of fixing the virtual entity if the user does not react (e.g., not providing user input) to the prompt asking or telling the user to engage in the activity of fixing the virtual entity. For example, the virtual entity may shout at or plead with the user rather than ask nicely if the user does not react to the prompt.

Input component 110 may be configured to obtain user input information defining user inputs, and/or other information. Input component 110 may obtain the user input information from computing platform(s) 140, external resource(s) 120, and/or other devices. In some implementations, input component 110 may obtain the user input information from the device associated with the computing platform(s) 140 and/or other devices. For example, the input component may obtain the user input information from the smart home device (e.g., smart speakers) and/or other devices associated with computing platform(s) 140. Input component 110 may obtain the user input information captured by the input devices and/or other devices. The user input may specify one or more user instructions for interacting with the stimulus. The user input may specify one or more selections of the virtual objects within the topography of the simulated physical space. The user input may specify one or more selections of options to modify the one or more settings of the stimulus. The user input may define a user's interaction with computing platform(s) 140. The user input may include one or more of a body gesture input, touch gesture input, controller input, text input, audio input, movement input, and/or other inputs.

A user input may comprise one or more of a body gesture input received through the imaging device, motion capture device, and/or other devices/sensors of computing platform(s) 140, one or more of a touch gesture input received through touch-enabled input device (e.g., a touch screen) of computing platform(s) 140, one or more of a controller input received through input device (e.g., a mouse, a keyboard, and/or a game controller) of computing platform(s) 140, an audio input received through an audio sensor of computing platform(s) 140, and/or other inputs revived through other devices.

The body gesture input may include information defining movement of a body part of the user, including movement of a hand, arm, leg, and/or other body parts of the user. The body gesture input may specify one or more selections of the virtual objects within the topography of the simulated physical space. The body gesture input may specify one or more selections of options to modify the one or more settings of the stimulus. The body gesture input may define a user's interaction with computing platform(s) 140.

In some implementations, the user's body gesture input may be interpreted from a video content through image-processing techniques, computer vision techniques, and/or other techniques. In some implementations, the image-processing techniques may include one or more of a bundle adjustment, SURF (Speeded-Up Robust Features), ORB (Oriented FAST and rotated BRIEF), computer vision, and/or other techniques. The computer vision techniques may include one or more recognition techniques, motion analysis techniques, image restoration techniques, and/or other techniques.

The touch gesture input may include information defining one or more movements. The movements may include one or more of a finger press, a finger tap, a finger swipe, a finger flick, a finger drag, a pinch, a touch-and-hold, a scroll, and/or other finger movements. These movements may similarly be carried out using a tool, such as a stylus. The touch gesture input may specify one or more selections of the virtual objects within the topography of the simulated physical space. The touch gesture input may specify one or more selections of options to modify the one or more settings of the stimulus. The touch gesture input may draw one or more images and/or trace one or more lines on the simulated physical space. The touch gesture input may define a user's interaction with computing platform(s) 140.

The controller input may include information defining one or more of a key/button pressing input, a key/button tapping input, a swiping input, a flick input, a drag input, a key/button press-and-hold input, a scroll input, and/or other inputs from a controller. The controller input may include one or more of a movement of a mouse, a movement of a mouse while holding a button on the mouse, a press of one or more keys of a keyboard, a movement of a joystick, a movement of a joystick while holding of a button on a controller, and/or other controller inputs. The controller input may specify one or more selections of the virtual objects within the topography of the simulated physical space. The controller input may specify one or more selections of options to modify the one or more settings of the stimulus. The controller input may define a user's interaction with computing platform(s) 140.

In some implementations, the text input may be obtained from a keyboard, a voice recognition device, and/or other devices. The text input may include one or more words in one or more languages. The one or more words may form one or more sentences in one or more languages.

The audio input may include information defining audio signals of a user. The audio signal of the user may be captured by a microphone and/or other audio capture devices. The audio signals from the user may be a voice command. In some implementations, instructions may be associated with the voice commands. The audio input may include the user singing a song, speaking one or more words, and/or other audio inputs. The audio input may have one or more of an audio duration defining a length of the audio input, an audio level defining a volume of the audio input, and/or other audio features. The association between the instructions and the voice command may be predetermined. The association between the instructions and the voice command may be determined by one or more machine learning techniques and/or other techniques.

The movement input may include information defining movements of computing platform(s) 140 and/or other devices. The movements may include a shaking movement, a projection movement, a rotation movement, and/or other movements. The shaking movement may include a user shaking computing platform(s) 140 and/or other devices. The projection movement may include a user throwing, tossing, and/or dropping computing platform(s) 140 and/or other devices. The rotation movement may include a user rotating computing platform(s) 140 and/or other devices about one or more axes. The movement input may be captured by one or more inertial measurement units, gyroscopes, and/or other motion sensing devices.

The user inputs may include an attempt to satisfy the set of task criteria for completing a task. The user input may specify instructions to manipulate the one or more virtual objects positioned throughout the topography of the simulated physical space. The instructions to manipulate the one or more virtual objects may include an attempt to satisfy the set of task criteria for completing the task.

For example, the task may be to fix the virtual entity by placing virtual objects (such as tape) on the virtual entity. The set of task criteria may specify the location within the simulated physical space and/or the virtual entity to place the virtual objects, the number of virtual objects required to fix the virtual entity, and/or other criteria. The user may attempt to satisfy the set of task criteria for completing the task by manipulating and/or placing the virtual objects at the location within the simulated physical space and/or the virtual entity specified by the set of task criteria through user input.

In some implementations, the set of task criteria for completing the task may require the user to move a body part in a particular manner. The user may input body gesture input in an attempt to satisfy the set of task criteria for completing the task. In some implementations, the set of task criteria for completing the task may require the user to input a particular touch gesture. The user may input touch gesture input in an attempt to satisfy the set of task criteria for completing the task. In some implementations, the set of task criteria for completing the task may require the user to submit a text input of a word phrase. The user may input text input in an attempt to satisfy the set of task criteria for completing the task. In some implementations, the set of task criteria for completing the task may require the user to say a word phrase. The user may input audio input in an attempt to satisfy the set of task criteria for completing the task.

Determination component 112 may be configured to determine whether the one or more criteria of the set of task criteria have been satisfied and/or other information. Determination component 112 may be configured to determine whether the one or more criteria of the set of task criteria has been satisfied based on the user input information and/or other information. Determination component 112 may determine whether the user input defined by the user input information satisfies the one or more criteria of the set of task criteria. Determination component 112 may be configured to identify a user input based on the user input information and/or other information.

Determination component 112 may determine whether the user input satisfies the one or more criteria of the set of task criteria by comparing the user input with the one or more criteria of the set of task criteria. If a user input matches a criterion from the set of task criteria, determination component 112 may determine that the criterion from the set of task criteria may be satisfied. If all the criteria from the set of task criteria have been satisfied, determination component 112 may determine that the set of task criteria has been satisfied.

For example, the task may be to fix the virtual entity by placing virtual objects (such as virtual object of tape) on the virtual entity. The set of task criteria may specify the location within the simulated physical space and/or the virtual entity to place the virtual objects, the number of virtual objects required to fix the virtual entity, and/or other criteria. The user may attempt to satisfy the set of task criteria by manipulating and/or placing the virtual objects at the location within the simulated physical space and/or the virtual entity specified by the set of task criteria through user input. Determination component 112 may identify the location of the virtual objects placed by the user based on the user input. Determination component 112 may determine whether the virtual objects placed by the user may be located at the location within the simulated physical space and/or the virtual entity specified by the set of task criteria. If the virtual objects placed by the user may be located at the location within the simulated physical space and/or the virtual entity specified by the set of task criteria, determination component 112 may determine that the set of task criteria may be satisfied and the task complete. If the virtual objects placed by the user are not located at the location within the simulated physical space and/or the virtual entity specified by the set of task criteria, determination component 112 may determine that the set of task criteria may be not satisfied and the task not complete.

By way of non-limiting example, a criterion of the set of task criteria for a puzzle may require a user to submit one or more text inputs. The user may submit the one or more text inputs through the input device of computing platform(s) 140. The one or more text inputs may be defined by user input information generated by the input device of computing platform(s) 140. Determination component 112 may determine whether the user input satisfies the criterion of the set of task criteria requiring the user to submit one or more text inputs. Responsive to the one or more text inputs matching the required one or more text inputs, determination component 112 may determine that the criterion of the set of task criteria may be satisfied.

For example, the set of task criteria may include a first criterion to select a first word from a word search puzzle, a second criterion to select a second word from the word search puzzle, and/or other criteria for the set of task criteria of a puzzle. Determination component 112 may determine whether the user input selected the first word from the word search puzzle, the second word from the word search puzzle, and/or other user inputs. Responsive to the determination component 112 identifying the user input selecting the first word from the word search puzzle, the second word from the word search puzzle, and/or other user inputs, determination component 112 may determine that the one or more criteria of the set of task criteria have been satisfied.

Determination component 112 may determine whether the one or more criteria of the set of task criteria based on occurrences within the real-world and/or the virtual world. Determination component 112 may be configured to obtain information defining occurrences within the real-world and/or virtual-world from computing platform(s) 140, external resource(s) 120, and/or other devices. In some implementations, a criterion of the set of task criteria may require an occurrence of an event within the real-world and/or the virtual world. Responsive to the determination component 112 obtaining information defining the occurrence of the event within the real-world and/or the virtual world, determination component 112 may determine that the criterion of the set of task criteria may be satisfied. Aforementioned, the user may or may not cause the occurrence of the event.

For example, a criterion of the set of task criteria may require a virtual entity within a game to be at a specific location within the topography of a simulated physical space. Determination component 112 may be configured to obtain information defining occurrences within the game from computing platform(s) 140, external resource(s) 120, and/or other devices. Responsive to the determination component 112 obtaining information indicating that the virtual entity within the game may be at the specific location within the topography of a simulated physical space, determination component 112 may determine that the criterion of the set of task criteria may be satisfied.

In some implementations, determination component 112 may be configured to determine whether the user input attempts to satisfy the one or more criteria of the set of task criteria. In some implementations, the user input may not include attempts to satisfy the one or more criteria of the set of task criteria. For example, if a criterion of the set of task criteria requires a text input and the user input does not provide a text input, determination component 112 may determine that the user input does not attempt to satisfy the set of task criteria. If the user input provides a text input, determination component 112 may determine that the user input does attempt to satisfy the set of task criteria.

Reconfiguration component 114 may be configured to modify the stimulus based on whether the one or more criteria of the set of task criteria has been satisfied. In some implementations, responsive to the set of task criteria being satisfied, reconfiguration component 114 may modify the stimulus by ceasing the presentation of the stimulus. Reconfiguration component 114 may cease the presentation of the stimulus on computing platform(s) 140 and/or other devices. Reconfiguration component 114 may transmit information to computing platform(s) 140 and/or other devices to cease the presentation of the stimulus. In some implementations, to cease presentation of the stimulus may include an end to the presentation of the visual content and/or audio content. In some implementations, to cease presentation of the stimulus may include an end to the presentation of the audio notification. For example, responsive to the user satisfying the set of task criteria for fixing the virtual entity with holes, reconfiguration component 114 may be configured to modify the stimulus such that the holes on the virtual entity may be removed, and the audio signal of the leaking air ceased.

In some implementations, responsive to the set of task criteria being satisfied, reconfiguration component 114 may modify the stimulus by altering the content of the stimulus. Reconfiguration component 114 may alter the content within stimulus by modifying the visual content and/or audio content, the task, the set of task criteria, the level of difficulty of the task, and/or other modifications. Reconfiguration component 114 may alter the content of the stimulus based on the criteria of the set of task criteria being satisfied. For example, responsive to a first criterion of the set of task criteria being satisfied, reconfiguration component 114 may cease the presentation of the stimulus. Responsive to a second criterion of the set of task criteria being satisfied, reconfiguration component 114 may cease the presentation of the stimulus for a duration of time. Reconfiguration component 114 may alter the content of the stimulus based on user input.

In some implementations, responsive to the set of task criteria being satisfied, reconfiguration component 114 may modify the stimulus by altering the content within stimulus based on user input. Reconfiguration component 114 may be configured to facilitate presentation of one or more options to modify the stimulus presented on computing platform(s) 140 and/or other devices. The user may select one or more of the options to modify the stimulus on computing platform(s) 140 and/or other devices. Responsive to a user selection of the one or more options to modify the stimulus, reconfiguration component 114 may be configured to facilitate the modification of the stimulus based on the user selection of the one or more options. The one or more options to modify the stimulus may be based on information defining the one or more settings of the stimulus.

The one or more options may include an option to cease presentation of the stimulus, an option to temporally cease presentation of the stimulus for a duration of time, an option to modify the task, an option to modify the set of task criteria, an option to modify the level of difficulty of the task, an option to modify the trigger criteria, and/or other options. Reconfiguration component 114 may be configured to facilitate the modification of the information defining the stimulus stored in electronic storage(s) 122, non-transitory storage media, and/or other storage media. Reconfiguration component 114 may be configured to facilitate the modification of the information defining the settings of the stimulus stored in electronic storage(s) 122, non-transitory storage media, and/or other storage media. Reconfiguration component 114 may be configured to facilitate the modification of the trigger information, the virtual content information, the task information, and/or other information defining the settings of the stimulus stored in electronic storage(s) 122, non-transitory storage media, and/or other storage media. In some implementations, an option to modify the stimulus may include ceasing presentation of the stimulus for a duration of time and presenting the stimulus with a different task and/or other modifications.

In some implementations, reconfiguration component 114 may be configured to modify the stimulus responsive to the user not attempting to satisfy the one or more criteria of the set of task criteria. Reconfiguration component 114 may modify the stimulus to encourage the user to satisfy the one or more criteria of the set of task criteria. Reconfiguration component 114 may modify the stimulus to encourage the user to satisfy the one or more criteria of the set of task criteria by providing the user with a reward. For example, the reward may include a monetary reward for a real-world environment and/or virtual world environment. In some implementations, the reward may be a virtual item for the virtual world environment. Reconfiguration component 114 may modify the stimulus to facilitate presentation of the reward. A reward that may be provided to a user to encourage the user to satisfy the one or more criteria of the set of task criteria may be random. In some implementations, the reward may be provided to the user when the user satisfies the one or more criteria of the set of task criteria. In some implementations, a preview of the reward may be provided to the user when the user may not be engaging the activity. In some implementations, a preview of the reward may be provided to the user when the user attempts to satisfy the one or more criteria of the set of task criteria. In some implementations, a preview of the reward may be provided to the user when the user fails to satisfy the one or more criteria of the set of task criteria.

In some implementations, reconfiguration component 114 may modify the stimulus to encourage the user to satisfy the one or more criteria of the set of task criteria by continuing the presentation of the stimulus. Reconfiguration component 114 may modify the stimulus to encourage the user to satisfy the one or more criteria of the set of task criteria by continuing the presentation of the stimulus with different settings of the stimulus. For example, responsive to the user not attempting to satisfy the one or more criteria of the set of task criteria, reconfiguration component 114 may be configured to modify the stimulus by increasing the volume of the audio content, increasing the frequency of the audio content, increase or decrease the level of difficulty of the stimulus, and/or other modifications. In some implementations, responsive to the user not attempting to satisfy the one or more criteria of the set of task criteria, reconfiguration component 114 may be configured to modify the stimulus by increasing the level of difficulty of the stimulus.

In some implementations, reconfiguration component 114 may be configured to modify the stimulus responsive to the user attempting to satisfy the one or more criteria of the set of task criteria. For example, responsive to the user attempting to satisfy the one or more criteria of the set of task criteria, reconfiguration component 114 may be configured to modify the stimulus by reducing the volume of the audio content, decrease the frequency of the audio content, increase or decrease the level of difficulty of the stimulus, and/or other modifications. In some implementations, reconfiguration component 114 may be configured to modify the stimulus to provide the user with a reward responsive to the user attempting to satisfy the one or more criteria of the set of task criteria. The reward that may be provided to a user responsive to the user attempting to satisfy the one or more criteria of the set of task criteria may be random.

In some implementations, reconfiguration component 114 may be configured to modify the one or more systems in the home associated with the smart home device and/or other devices. Reconfiguration component 114 may be configured to facilitate modification of the lighting system, the air conditioning system, the heating system, and/or other home systems. Responsive to the one or more criteria of the set of task criteria being satisfied, reconfiguration component 114 may facilitate modification of the lighting system, the air conditioning system, the heating system, and/or other home systems. For example, responsive to the set of task criteria being satisfied, reconfiguration component 114 may be configured facilitate the brightening or dimming of the lights, increasing or decreasing the temperature in the air conditioning system and/or heating system, and/or other modifications in other home systems.

In some implementations, reconfiguration component 114 may be configured to modify the one or more systems in the home associated with the smart home device base on the criterion satisfied in the set of task criteria. For example, responsive to the first criterion being satisfied, reconfiguration component 114 may be configured facilitate modification of a first home system, responsive to the second criterion being satisfied, reconfiguration component 114 may be configured facilitate modification of a second home system, and/or responsive to the other criteria being satisfied, reconfiguration component 114 may be configured facilitate modification of other home systems. The first home system may be the lighting system and/or other systems. The second home system may be the heating system and/or other systems.

By way of non-limiting illustration, responsive to the first criterion being satisfied, reconfiguration component 114 may be configured facilitate the brightening of the lights. Responsive to the second criterion being satisfied, reconfiguration component 114 may be configured facilitate the decreasing the temperature of the air conditioning system and/or heating system.

In some implementations, server(s) 102, computing platform(s) 140, and/or external resource(s) 120 may be operatively linked via one or more electronic communication links. For example, such electronic communication links may be established, at least in part, via a network 103 such as the Internet and/or other networks. It will be appreciated that this is not intended to be limiting, and that the scope of this disclosure may include implementations in which server(s) 102, computing platform(s) 140, and/or external resource(s) 120 may be operatively linked via some other communication media.

In some implementations, external resource(s) 120 may include sources of information, hosts and/or providers of virtual environments outside of system 100, external entities participating with system 100, and/or other resources. In some implementations, some or all of the functionality attributed herein to external resource(s) 120 may be provided by resources included in system 100.

In some implementations, Server(s) 102 may include electronic storage(s) 122, processor(s) 124, and/or other components. Server(s) 102 may include communication lines or ports to enable the exchange of information with a network and/or other computing devices. Illustration of server(s) 102 in FIG. 1 is not intended to be limiting.

Server(s) 102 may include a plurality of hardware, software, and/or firmware components operating together to provide the functionality attributed herein to server(s) 102. For example, server(s) 102 may be implemented by a cloud of computing devices operating together as server(s) 102.

In some implementations, electronic storage(s) 122 may include electronic storage media that electronically stores information. The electronic storage media of electronic storage(s) 122 may include one or both of system storage that is provided integrally (i.e., substantially nonremovable) with server(s) 102 and/or removable storage that is removably connectable to server(s) 102 via, for example, a port (e.g., a USB port, a firewire port, etc.) or a drive (e.g., a disk drive, etc.). Electronic storage(s) 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage(s) 122 may include one or more virtual storage resources (e.g., cloud storage, a virtual private network, and/or other virtual storage resources). Electronic storage(s) 122 may store software algorithms, information determined by processor(s) 124, information received from server(s) 102, information received from computing platform(s) 140, and/or other information that enables server(s) 102 to function as described herein.

In some implementations, processor(s) 124 may be configured to provide information processing capabilities in server(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same computing platform, or processor(s) 124 may represent processing functionality of a plurality of devices operating in coordination. The processor(s) 124 may be configured to execute computer-readable instruction components 106, 108, 110, 112, 114, and/or other components. The processor(s) 124 may be configured to execute components 106, 108, 110,112, 114, and/or other components by software; hardware; firmware; some combination of software, hardware, and/or firmware; and/or other mechanisms for configuring processing capabilities on processor(s) 124.

It should be appreciated that although components 106, 108, 110, 112, and 114 are illustrated in FIG. 1 as being co-located within a single processing unit, in implementations in which processor(s) 124 may include multiple processing units, one or more of components 106, 108, 110, 112, and/or 114 may be located remotely from the other components. The description of the functionality provided by the different components 106, 108, 110, 112, and/or 114 described herein is for illustrative purposes, and is not intended to be limiting, as any of components 106, 108, 110, 112, and/or 114 may provide more or less functionality than is described. For example, one or more of components 106, 108, 110, 112, and/or 114 may be eliminated, and some or all of its functionality may be provided by other ones of components 106, 108, 110, 112, and/or 114. As another example, processor(s) 124 may be configured to execute one or more additional components that may perform some or all of the functionality attributed herein to one of components 106, 108, 110, 112, and/or 114.

Figure 2:
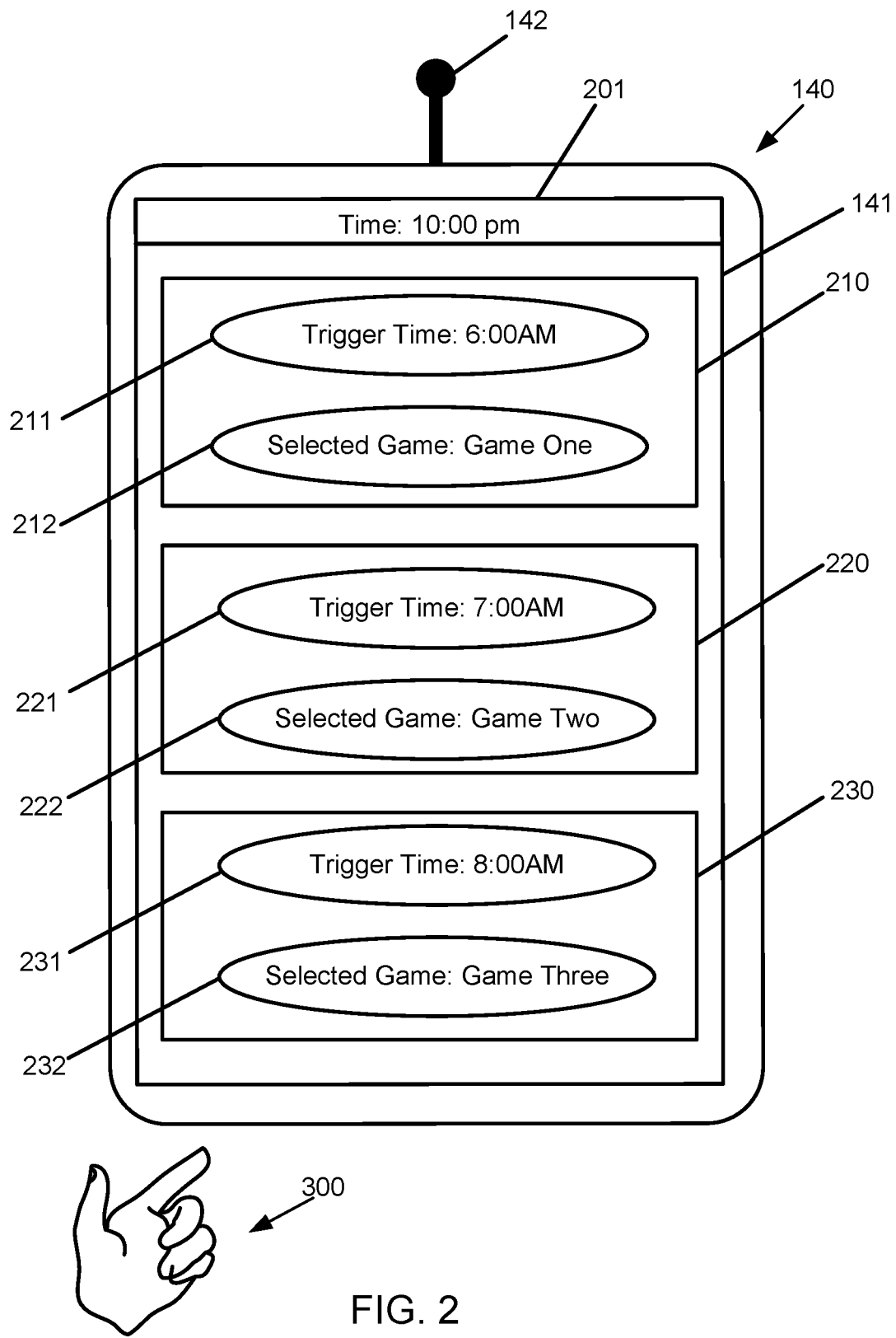
FIG. 2 illustrates a depiction of a computing platform showing one or more settings for one or more stimuli, in accordance with one or more implementations.

As is illustrated in FIG. 2 depicts a user determining one or more settings of one or more stimulus on computing platform(s) 140. A user 300 may be determining the one or more settings of one or more stimulus on computing platform(s) 140. User 300 may determine the one or more settings at time 201. Time 201 may be 10 pm. User 300 may determine the one or more settings prior to the presentation of the one or more stimulus. The one or more stimulus may include a first stimulus 210, a second stimulus 220, a third stimulus 230, and/or other stimuli. One or more options for the one or more settings of the one or more stimulus may be presented on touch-enabled display 141. The first stimulus 210 may include options for a first trigger time 211, a first task 212, and/or other options. First trigger time 211 may specify the time when first task 212 may be presented on computing platform(s) 140. First task 212 may specify the task including a first set of task criteria presented on computing platform(s) 140. The second stimulus 220 may include options for a second trigger time 221, a second task 222, and/or other options. Second trigger time 221 may specify the time when second task 222 may be presented on computing platform(s) 140. Second task 222 may specify the task including a second set of task criteria presented on computing platform(s) 140. The third stimulus 230 may include options for a third trigger time 231, a third task 232, and/or other options. Third trigger time 231 may specify the time when third task 232 may be presented on computing platform(s) 140. Third task 232 may specify the task including a third set of task criteria presented on computing platform(s) 140. User 300 may modify first trigger time 211, first task 212, second trigger time 221, second task 222, third trigger time 231, third task 232, and/or other options. User 300 may modify the set of task criteria of the first task 212, second task 222, third task 232, and/or other tasks.

Figure 3:
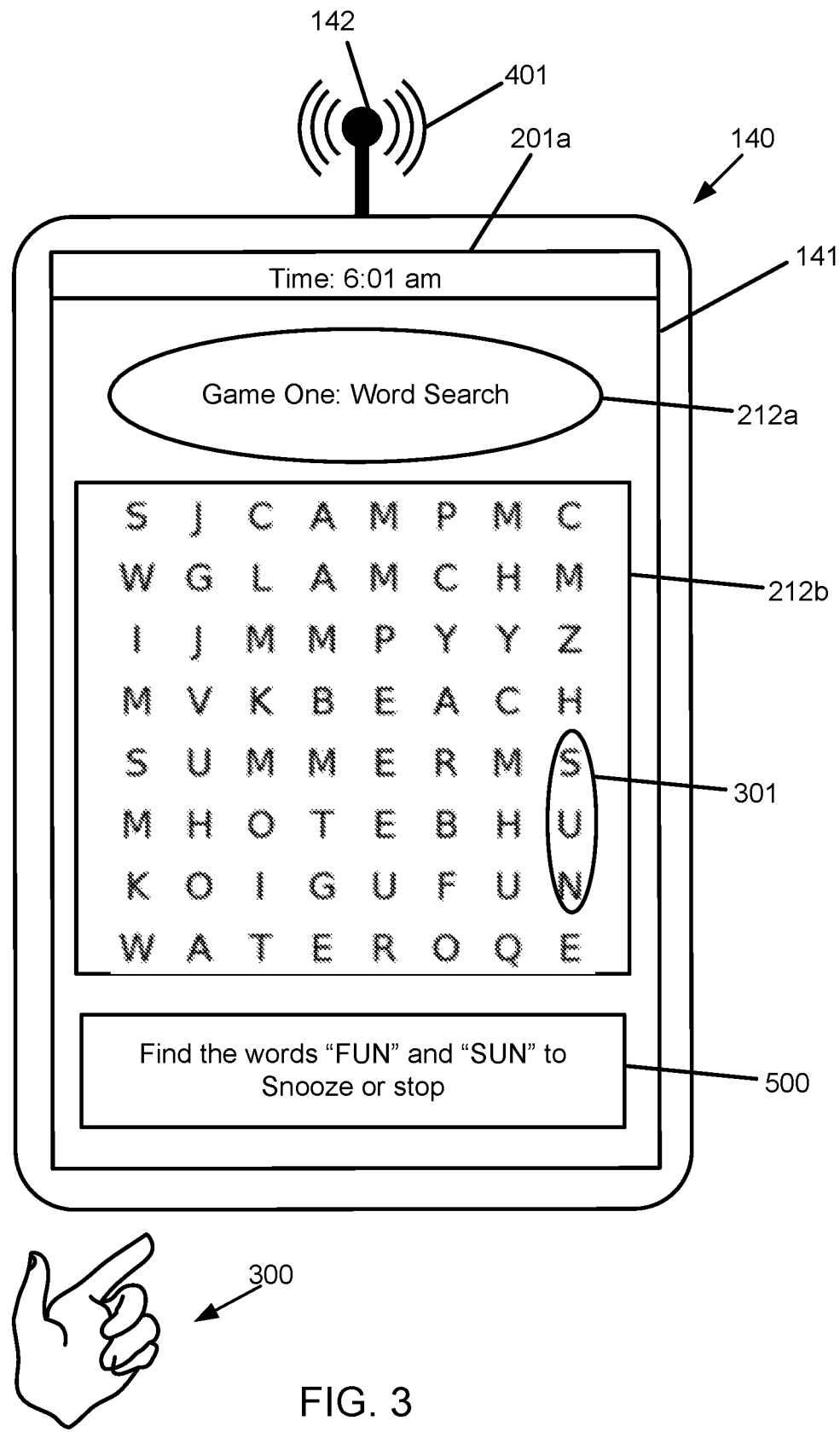
FIG. 3 illustrates a depiction of a first stimulus including a task having a set of task criteria presented on a computing platform, in accordance with one or more implementations.

As is illustrated in FIG. 3 depicts a presentation of first stimulus 210 (references in FIG. 2) including the task 212a on touch-enabled display 141 of computing platform(s) 140. First trigger time 211 may specify a time when first task 212 may be presented on computing platform(s) 140. Responsive to first trigger time 211 being satisfied, first stimulus 210 may be presented. Time 201a may satisfy first trigger time 211. Presentation of first stimulus 210 may include presentation of visual content depicted on touch-enabled display 141 and presentation of audio content by an audio output device 142. The presentation of audio content by an audio output device 142 may include the generation of a first audio notification 401. First audio notification 401 may prompt user 300 to engage with task 212a or the content presented on touch-enabled display 141. First audio notification 401 may be presented at a first audio volume.

Task 212a may be specified by first task 212. Task 212a may be a word search puzzle. The word search puzzle may include a depiction of a simulated physical space 212b, one or more virtual objects, and/or other content. The virtual objects may be the letters positioned throughout the topography of simulated physical space 212b. A first set of task criteria 500 may specify a condition for completing task 212a. First set of task criteria 500 may be presented on touch-enabled display 141 of computing platform(s) 140. By way of non-limiting example, the criteria for satisfying first set of task criteria 500 may include finding/select the words "FUN" and "SUN" in the word search puzzle. User 300 may attempt to satisfy first set of task criteria 500 by inputting a first user input 301 on touch-enabled display 141. First audio notification 401 may be presented until first set of task criteria 500 is satisfied.

Figure 4:
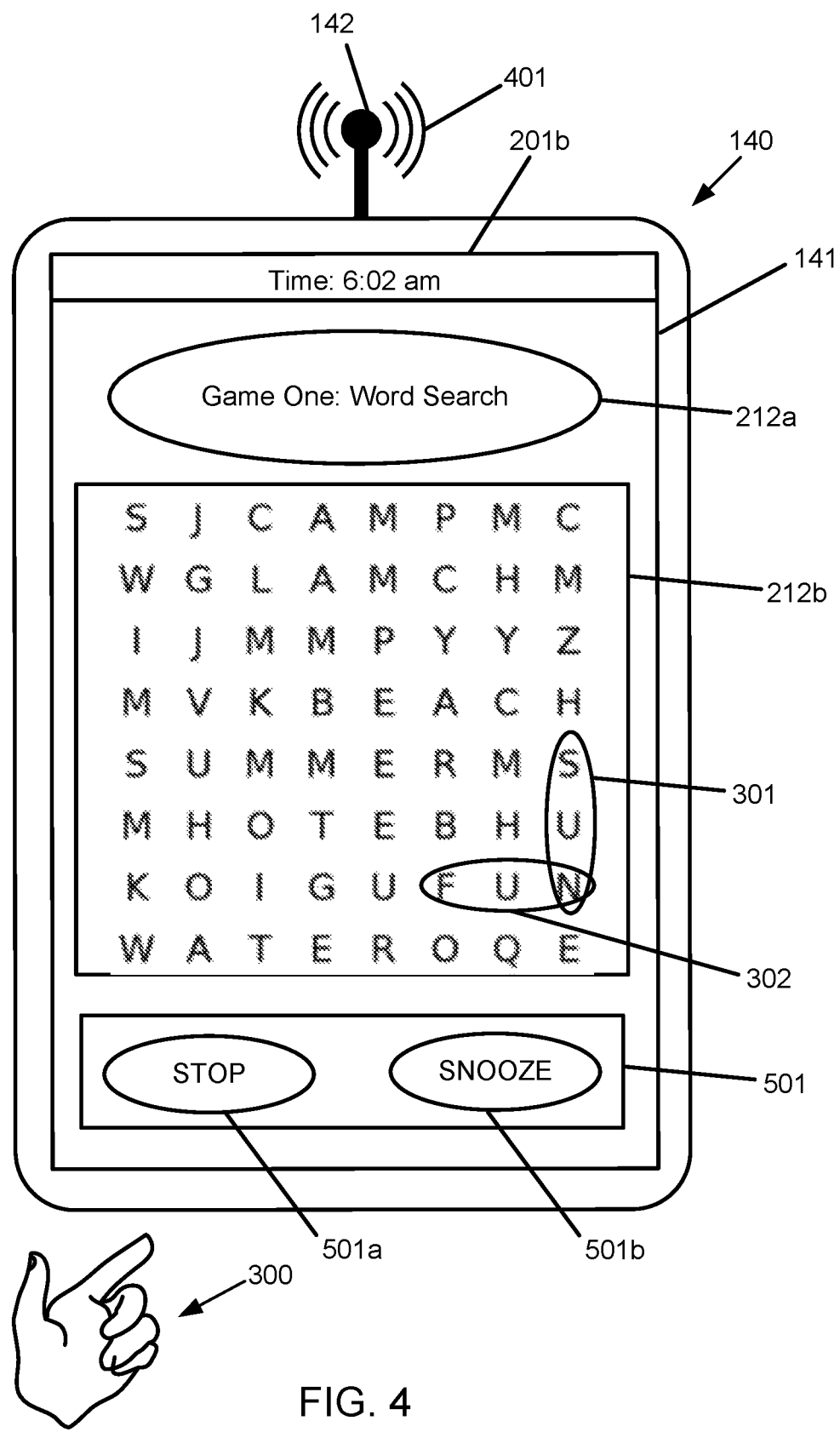
FIG. 4 illustrates a depiction of a user satisfying the set of task criteria of the task of the first stimulus presented on a computing platform, in accordance with one or more implementations.

As is illustrated in FIG. 4 depicts user 300 satisfying first set of task criteria 500 for completing task 212a at time 201b. User 300 may satisfy first set of task criteria 500 for completing task 212a by inputting a first user input 301 and a second user input 302. The criteria for satisfying first set of task criteria 500 may include finding/select the words "FUN" and "SUN" in the word search puzzle. First user input 301 selects the word "SUN" and second user input 302 selects the word "FUN." Responsive to the first set of task criteria 500 being satisfied, user 300 may be presented with options 501 to modify first stimulus 210. Options 501 may include a first option 501a to cease the presentation of first stimulus 210, a second option 501b to cease the presentation of first stimulus 210 for a short duration of time, and/or other options.

Figure 5:
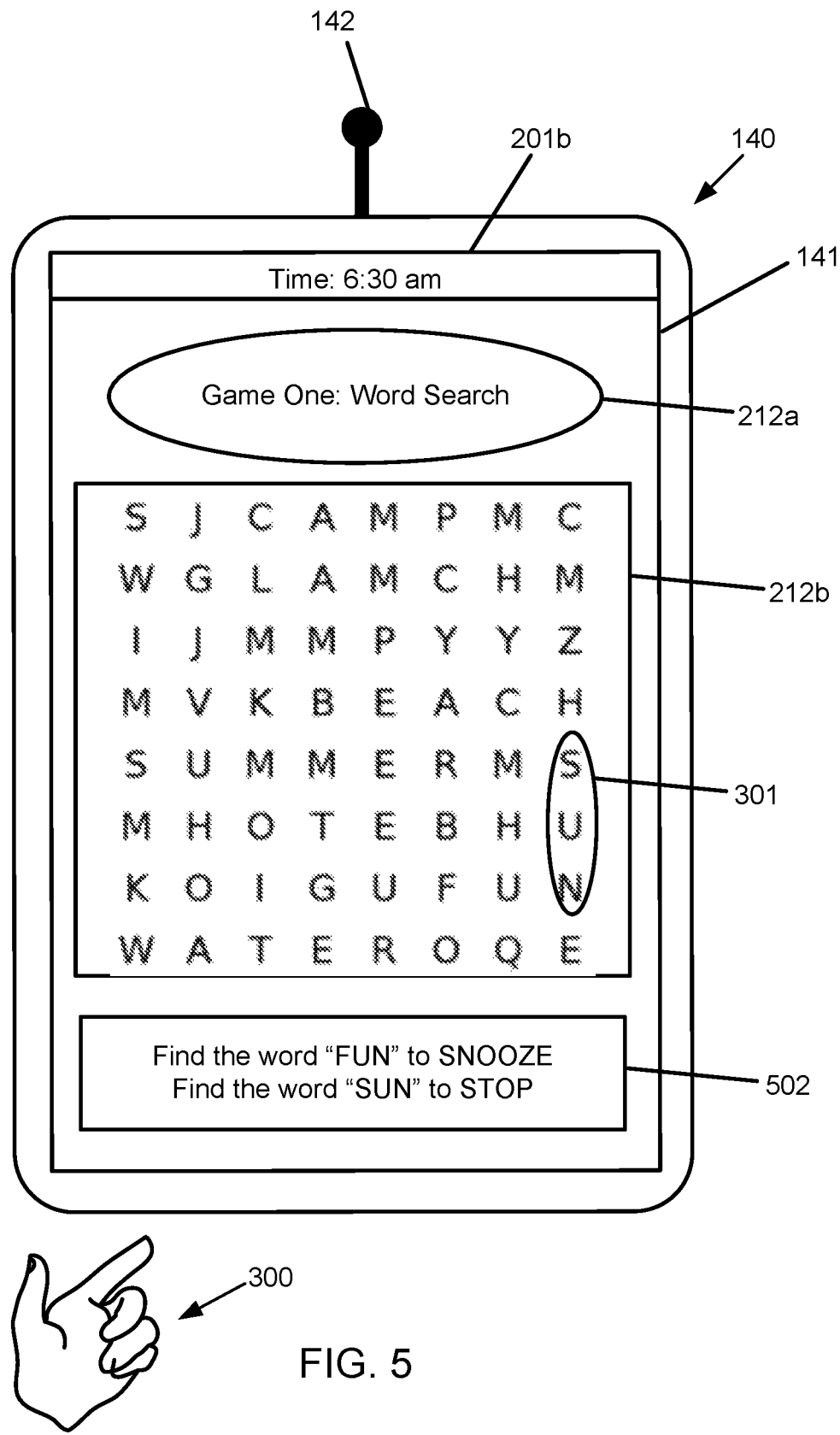
FIG. 5 illustrates a depiction of the first stimulus being ceased as a result of the user satisfying the set of task criteria of the task of the first stimulus, in accordance with one or more implementations.

As is illustrated in FIG. 5 depicts a presentation of first stimulus 210 including the task 212a on touch-enabled display 141 of computing platform(s) 140 with a second set of task criteria 502 at time 201b. Second set of task criteria 502 may be presented in response to a user selecting second option 201b. For example, user 300 may choose to delay the presentation of first stimulus 210 for a duration of time (e.g., snooze). Responsive to the end of the delay, first stimulus 210 may be presented with second set of task criteria 502. Second set of task criteria 502 may include one or more options for modifying first stimulus 210. A criterion of second set of task criteria 502 may be to find/select the word "FUN." Responsive to user 300 selecting the word "FUN," the presentation of first stimulus 210 may cease for a short duration of time. A criterion of second set of task criteria 502 may be to find/select the word "SUN." Responsive to user 300 selecting the word "SUN," the presentation of first stimulus 210 may cease. Ceasing presentation of first stimulus 210 may include the end of the presentation of first audio notification 401 by audio output device 142.

Figure 6:
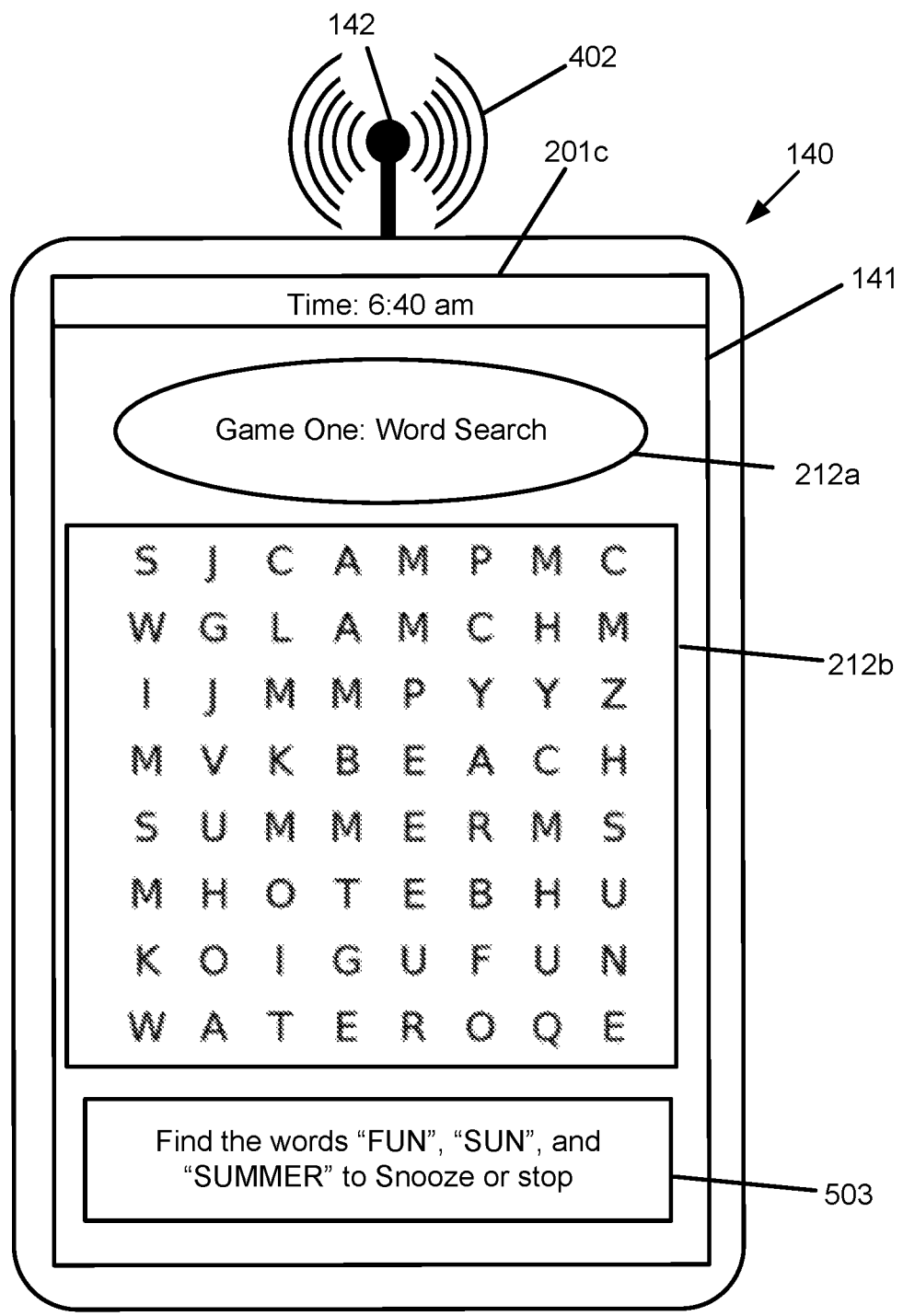
FIG. 6 illustrates a depiction of the user not attempting to satisfying the set of task criteria of the task of the first stimulus and the stimulus being modified, in accordance with one or more implementations.

As is illustrated in FIG. 6 depicts an example of user 300 not reacting and/or providing input in response to the presentation of first stimulus 210 at time 201c. Responsive to user 300 not reacting and/or providing input in response to the presentation of first stimulus 210, first stimulus 210 may be modified to encourage user 300 to react and/or provide input. First stimulus 210 may be modified by effectuating a second audio notification 402 and modifying first set of task criteria 500 with a third set of task criteria 503. Second audio notification 402 may have a greater audio volume compared to first audio notification 401. Second audio notification 402 may have a different audio content compared to first audio notification 401. For example, first audio notification 401 may ask the user nicely to react to first stimulus 210, and second audio notification 402 may yell at the user to react to first stimulus 210. Third set of task criteria 503 may be more difficult compared to first set of task criteria 500. For example, third set of task criteria 503 may require the user to find/select three words rather than two words to be presented with options 501.

As is illustrated in FIG. 7 depicts a presentation of second stimulus 220 including the task 222a on touch-enabled display 141 of computing platform(s) 140. Second trigger time 221 may specify a time when second task 222 may be presented on computing platform(s) 140. Responsive to second trigger time 221 being satisfied, second stimulus 220 may be presented. Time 201d may satisfy second trigger time 221. Presentation of second stimulus 220 may include presentation of visual content depicted on touch-enabled display 141 and presentation of audio content by an audio output device 142. The presentation of audio content by an audio output device 142 may include the generation of a second audio notification 401a. Second audio notification 401a may prompt user 300 to engage with task 222a or the content presented on touch-enabled display 141. Second audio notification 401a may include audio signal of leaking air.

Task 222a may be specified by second task 222. Task 222a may involve a game of fixing virtual object 400. Virtual object 400 may be a representation of a balloon that is leaking air. Virtual object 400 may be positioned in a simulated physical space 222b. Simulated physical space 222b may be an environment to play the game of fixing virtual object 400. A fourth set of task criteria 504 may specify a condition for completing task 222a. Fourth set of task criteria 504 may be presented on touch-enabled display 141 of computing platform(s) 140. By way of non-limiting example, the criteria for satisfying fourth set of task criteria 504 may be to place virtual object 406 at the location of hole 402 to repair virtual object 400. Virtual object 406 may be a representation of a bandage. Hole 402 may be a representation of damage to virtual object 400. An animation 404 may be a representation of the air leaking from virtual object 400 and the location of hole 402. The audio signal of leaking air may be associated with animation 404. When virtual object 400 is repaired, the audio signal of leaking air that may be associated with animation 404 may cease. User 300 may attempt to satisfy first set of task criteria 500 by inputting a second user input 408 on touch-enabled display 141. Second audio notification 401a may be presented until fourth set of task criteria 504 is satisfied.

As is illustrated in FIG. 8, responsive to the user satisfying fourth set of task criteria 504 (illustrated in FIG. 7) by placing virtual object 406 at the location of hole 402 to repair virtual object 400. The second audio notification 401a including audio signal of leaking air may cease. User 300 may be presented with options 501 including first option 501a to cease the presentation of first stimulus 210, second option 501b to cease the presentation of first stimulus 210 for a short duration of time, and/or other options. User 300 may select one or more of the presented options in options 501.

Figure 9:
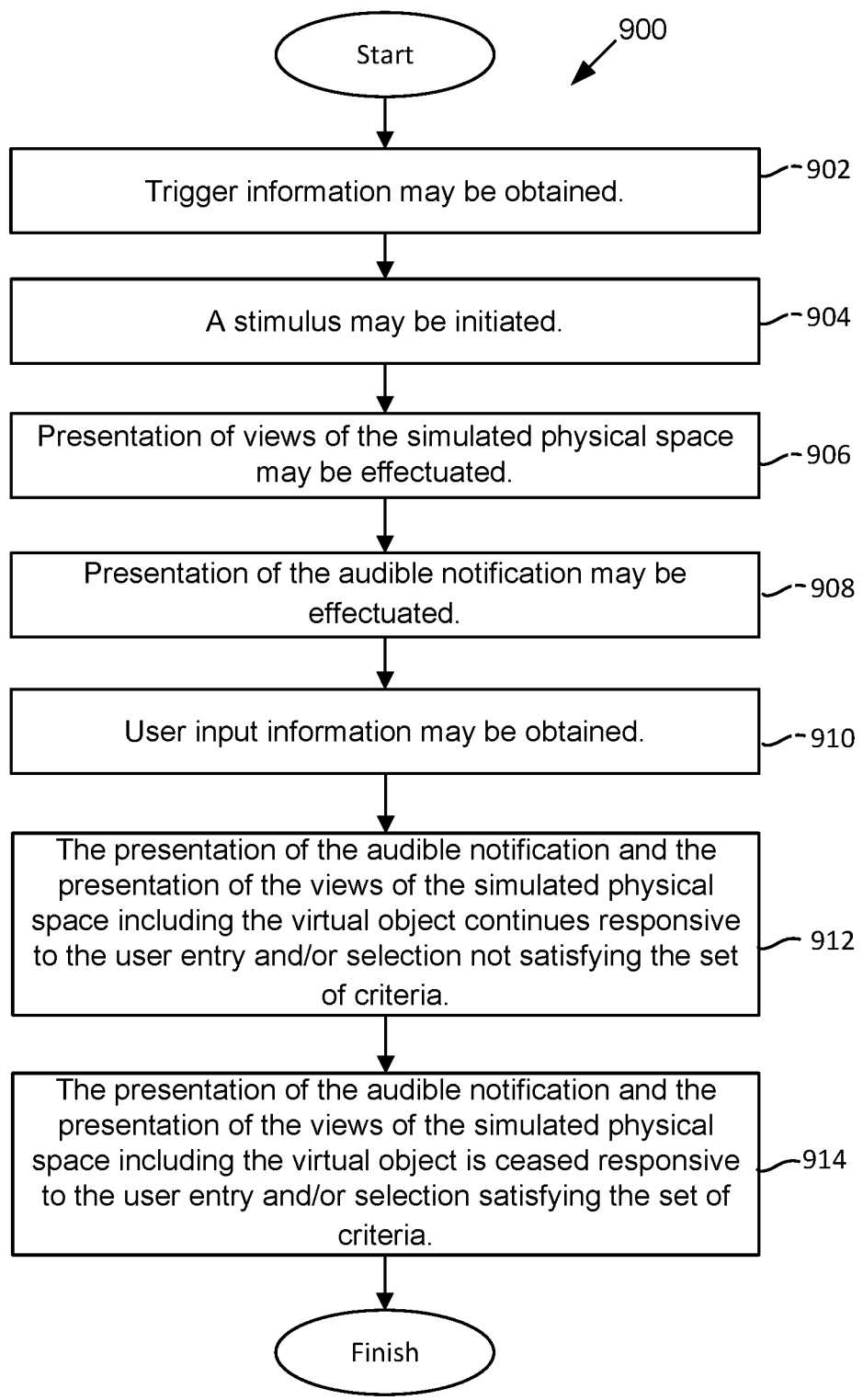
FIG. 9 illustrates a method configured to present a stimulus through a simulated physical space on a computing platform to elicit user interaction, in accordance with one or more implementations.

FIG. 9 illustrates the method 900, in accordance with one or more implementations. The operations of method 900 presented below are intended to be illustrative. In some implementations, method 900 may be accomplished with one or more additional operations not described, and/or without one or more of the operations discussed. Additionally, the order in which the operations of method 900 are illustrated in FIG. 9 and described below are not intended to be limiting.

In some implementations, method 900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At an operation 902, trigger information may be obtained. The trigger information may specify a trigger time for triggering a stimulus. The stimulus may include a presentation of a simulated physical space and an audible notification. In some embodiments, operation 902 may be performed by a configuration component the same as or similar to configuration component 106 (shown in FIG. 1 and described herein).

At an operation 904, the stimulus may be initiated at an occurrence of the trigger time. In some embodiments, operation 904 may be performed by a presentation component the same as or similar to presentation component 108 (shown in FIG. 1 and described herein).

At an operation 906, presentation of views of the simulated physical space may be effectuated. The simulated physical space may be effectuated on a display of a computing platform associated with a user. The simulated physical space may include a virtual object presented within a topography of the simulated physical space. The virtual object presents a task to the user. The presentation of the task to the user may include a prompt for the user to interact with the virtual object. The task may have a set of criteria for completing the task. In some embodiments, operation 906 may be performed by the presentation component the same as or similar to presentation component 108 (shown in FIG. 1 and described herein).

At an operation 908, presentation of the audible notification may be effectuated. the audible notification may be effectuated via an audio output device of the computing platform. The audible notification may prompt the user to interact with the virtual object. In some embodiments, operation 908 may be performed by the presentation component the same as or similar to presentation component 108 (shown in FIG. 1 and described herein).

At an operation 910, user input information may be obtained. The user input information may include user entry and/or selection of the virtual object within the virtual space. The user entry and/or selection may convey an attempt to satisfy the set of criteria for completing the task. In some embodiments, operation 910 may be performed by an input component the same as or similar to input component 110 (shown in FIG. 1 and described herein).

At an operation 912, the presentation of the audible notification and the presentation of the views of the simulated physical space including the virtual object continues. The presentation of the audible notification and the presentation of the views of the simulated physical space including the virtual object continues responsive to the user entry and/or selection not satisfying the set of criteria. In some embodiments, operation 912 may be performed by a determination component the same as or similar to determination component 112 (shown in FIG. 1 and described herein).

At an operation 914, the presentation of the audible notification and the presentation of the views of the simulated physical space including the virtual object may be ceased. The presentation of the audible notification and the presentation of the views of the simulated physical space including the virtual object may be ceased responsive to the user entry and/or selection satisfying the set of criteria. In some embodiments, operation 914 may be performed by a reconfiguration component the same as or similar to reconfiguration component 114 (shown in FIG. 1 and described herein).

Although the system(s) and/or method(s) of this disclosure have been described in detail for the purpose of illustration based on what is currently considered to be the most practical and/or preferred implementations, it is to be understood that such detail is solely for that purpose and/or that the disclosure is not limited to the disclosed implementations, but, on the contrary, is intended to cover modifications and/or equivalent arrangements that are within the spirit and/or scope of the appended claims. For example, it is to be understood that the present disclosure contemplates that, to the extent possible, one or more features of any implementation can be combined with one or more features of any other implementation.

What is claimed:

1. A system configured to elicit user interaction with a stimulus through a simulated physical space on a computing platform, the system comprising:
   one or more physical processors configured by machine-readable instructions to:
      obtain trigger information, the trigger information specifying a trigger time for triggering a stimulus, the stimulus including a presentation of the simulated physical space and an audible notification;
      at an occurrence of the trigger time, initiate the stimulus by:
         effectuating presentation of views of the simulated physical space on a display of a computing platform associated with a user, the simulated physical space includes a virtual object presented within a topography of the simulated physical space, the virtual object presents a task to the user, the presentation of the task to the user includes a prompt for the user to interact with the virtual object, the task having a set of criteria for completing the task; and
         effectuating presentation of the audible notification via an audio output device of the computing platform, the audible notification prompting the user to interact with the virtual object;
      obtaining user input information, the user input information including at least one of user entry or selection of the virtual object within the virtual space, the at least one of the user entry or the selection conveying an attempt to satisfy the set of criteria for completing the task;
      responsive to the at least one of the user entry or the selection not satisfying the set of criteria, continue the stimulus by continuing the presentation of the audible notification and the presentation of the views of the simulated physical space including the virtual object; and,
      responsive to the at least one of the user entry or the selection satisfying the set of criteria, end the stimulus by ceasing one or both of the presentation of the audible notification or the presentation of the views of the simulated physical space including the virtual object,
      wherein the presentation of the views of the simulated physical space including the virtual object continues over time, and a level of complexity of the set of criteria for completing the task increases with the time until the at least one of the user entry and/or the selection is obtained or the set of criteria is satisfied.

2. The system of claim 1, wherein the presentation of the audible notification via the audio output device of the computing platform continues over the time, and an audible intensity of the audible notification increases with the time until the set of criteria is satisfied.

3. The system of claim 1, wherein the level of complexity of the set of criteria is determined based on the amount of time the user previously took to satisfy a previous set of criteria, a number of attempts taken to satisfy the previous set of criteria, or a combination thereof.

4. The system of claim 1, wherein the audible notification is determined based on an interaction in a real-world environment, a geolocation, or a combination thereof.

5. The system of claim 4, wherein the interaction includes purchases made by the user, locations visited by the user, events attended by the user, conversations the user had, websites visited by the user, or a combination thereof.

6. The system of claim 1, wherein responsive to the at least one of the user entry or the selection satisfying the set of criteria, the one or more physical processors are further configured by machine-readable instructions to:
effectuate presentation of a set of instructions configured for user selection on the display of the computing platform;
obtain a selection of an individual instruction from the set of instructions; and
modify the stimulus based on the selected individual instruction.

7. The system of claim 1, wherein the virtual object depicts a virtual entity including visual cues that elicit the interaction by the user.

8. The system of claim 1, wherein the set of criteria for completing the task includes one or more of user entry of information, selection of a certain portion or portions of the simulated physical space, or selection of a certain portion or portions of the virtual object.

9. The system of claim 1, wherein the display is a touch-enabled display, and the at least one of the user entry or the selection includes a press, a tap, a swipe, a flick, a drag, a pinch, a touch-and-hold, scrolling, text entry, shake, or a combination thereof.

10. A method to elicit user interaction with a stimulus through a simulated physical space on a computing platform, the method comprising:
obtaining trigger information, the trigger information specifying a trigger time for triggering a stimulus, the stimulus including a presentation of the simulated physical space and an audible notification; and
at an occurrence of the trigger time, initiating the stimulus by:
effectuating presentation of views of the simulated physical space on a display of a computing platform associated with a user, the simulated physical space includes a virtual object presented within a topography of the simulated physical space, the virtual object presents a task to the user, the presentation of the task to the user includes a prompt for the user to interact with the virtual object, the task having a set of criteria for completing the task; and
effectuating presentation of the audible notification via an audio output device of the computing platform, the audible notification prompting the user to interact with the virtual object;
obtaining user input information, the user input information including at least one of user entry or selection of the virtual object within the virtual space, the at least one of the user entry or the selection conveying an attempt to satisfy the set of criteria for completing the task;
responsive to the at least one of the user entry or the selection not satisfying the set of criteria, continuing the presentation of the audible notification and the presentation of the views of the simulated physical space including the virtual object; and,
responsive to the at least one of the user entry or the selection satisfying the set of criteria, ending the stimulus by ceasing one or both of the presentation of the audible notification or the presentation of the views of the simulated physical space including the virtual object,
wherein the presentation of the views of the simulated physical space including the virtual object continues over time, and a level of complexity of the set of criteria for completing the task increases with the time until the user entry and/or selection is obtained or the set of criteria is satisfied.

11. The method of claim 10, wherein the presentation of the audible notification via the audio output device of the computing platform continues over the time, and an audible intensity of the audible notification increases with the time until the set of criteria is satisfied.

12. The method of claim 10, wherein the level of complexity of the set of criteria is determined based on the amount of time the user previously took to satisfy a previous set of criteria and/or a number of attempts taken to satisfy the previous set of criteria.

13. The method of claim 10, wherein the audible notification is determined based on an interaction in a real-world environment, a geolocation, or a combination thereof.

14. The method of claim 13, wherein the interaction includes purchases made by the user, locations visited by the user, events attended by the user, conversations the user had, websites visited by the user, or a combination thereof.

15. The method of claim 10, wherein responsive to the at least one of the user entry or the selection satisfying the set of criteria, the method further comprises of:
effectuating presentation of a set of instructions configured for user selection on the display of the computing platform;
obtaining a selection of an individual instruction from the set of instructions; and
modifying the stimulus based on the individual instruction.

16. The method of claim 10, wherein the virtual object depicts a virtual entity including visual cues that elicit the interaction by the user.

17. The method of claim 10, wherein the set of criteria for completing the task includes one or more of user entry of information, selection of a certain portion or portions of the simulated physical space, or selection of a certain portion or portions of the virtual object.

18. The method of claim 10, wherein the display is a touch-enabled display, and the at least one of the user entry or the selection includes a press, a tap, a swipe, a flick, a drag, a pinch, a touch-and-hold, scrolling, text entry, shake, or a combination thereof.

* * * * *